United States Patent
Wu

(10) Patent No.: US 10,441,612 B2
(45) Date of Patent: Oct. 15, 2019

(54) INTESTINAL MICROBE THERAPY, COMPOSITION THEREFOR AND METHOD FOR PREPARING THE SAME

(71) Applicant: Taichung Veterans General Hospital, Taichung (TW)

(72) Inventor: Chun-Ying Wu, Taichung (TW)

(73) Assignee: TAICHUNG VETERANS GENERAL HOSPITAL, Taichung (TW)

( * ) Notice: Subject to any disclaimer, the term of this patent is extended or adjusted under 35 U.S.C. 154(b) by 189 days.

(21) Appl. No.: 15/238,359

(22) Filed: Aug. 16, 2016

(65) Prior Publication Data

US 2018/0050069 A1    Feb. 22, 2018

(51) Int. Cl.
  *A61K 35/74*  (2015.01)
  *C12Q 1/689*  (2018.01)
  *A61K 35/12*  (2015.01)

(52) U.S. Cl.
  CPC .............. *A61K 35/74* (2013.01); *A61K 35/12* (2013.01); *C12Q 1/689* (2013.01); *C12Q 2600/118* (2013.01)

(58) Field of Classification Search
  None
  See application file for complete search history.

(56) References Cited

PUBLICATIONS

Davis "H. pylori Infection Symptoms, Test, and Treatment" MedicineNet.com, https://www.medicinenet.com/helicobacter_pylori/article.htm, 7pgs, accessed Jul. 22, 2018 (Year: 2018).*
UniProt "Taxonomy-bacterium A-F-12" 1pg accessed Jul. 22, 2018 (Year: 2018).*
Morgan et al. "Dysfunction of the intestinal microbiome in inflammatory bowel disease and treatment" Genome Biology 2012, 13:R79, 18 pgs (Year: 2012).*

* cited by examiner

*Primary Examiner* — Thane Underdahl
(74) *Attorney, Agent, or Firm* — Muncy, Geissler, Olds & Lowe, P.C.

(57) ABSTRACT

The present invention discloses a method for treating and/or preventing metabolic syndrome and related diseases thereof, by administering a microbe composition to an individual to achieve the modulation of blood glucose, inhibition of body weight gain, reduction of low density cholesterol in blood, and reduction of hepatic expression of inflammatory factors, thereby effectively treating and/or preventing metabolic syndrome or related diseases thereof.

10 Claims, 32 Drawing Sheets

Specification includes a Sequence Listing.

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: bar-coded universal primer 341F
<220> FEATURE:
<221> NAME/KEY: misc_feature
<222> LOCATION: (9)..(9)
<223> OTHER INFORMATION: n is a, c, g, or t

<400> SEQUENCE: 1
cctacgggng gcwgcag                                                  17

<210> SEQ ID NO 2
<211> LENGTH: 21
<212> TYPE: DNA
<213> ORGANISM: Artificial Sequence
<220> FEATURE:
<223> OTHER INFORMATION: bar-coded universal primer 805R

<400> SEQUENCE: 2
gactachcgg gtatctaatc c                                             21
```

INTESTINAL MICROBE THERAPY, COMPOSITION THEREFOR AND METHOD FOR PREPARING THE SAME

FIELD OF THE INVENTION

The present invention relates to an intestinal microbe therapy, and more particularly to the treatment and/or prevention of metabolic syndrome and related diseases thereof with intestinal microbe, as well as a composition for use in the therapy and a method for preparing the composition.

DESCRIPTION OF THE RELATED ART

Human gastrointestinal microorganisms include more than 1000 different bacterial species with more than 100 trillions in number, and thus the gastrointestinal microbiota has become a large part of human body structures, such that phenomena such as metabolism, immune response, and development of intestinal cells in human body all are closely linked to the gastrointestinal microbiota.

It has been found that different diet habits can result in differences in the composition of the gastrointestinal microbiota in individuals, and it has been further indicated that the gastrointestinal microbiota is involved in many diseases, and for example, in the gastrointestinal microbiota of a human or murine obesity mode, Bacteriodetes and Firmicutes are in the imbalanced condition. At present, it has been found that diseases related to the gastrointestinal microbiota include colitis, constipation, metabolic syndrome, and crohn's disease and so on, in addition to obesity.

In the past, for most diseases due to abnormalities in the gastrointestinal microbiota, antibiotics are used as treatment means. Although antibiotics can improve symptoms, the therapeutic effect cannot be maintained after drug withdrawal, and long-term use of antibiotics may not only result in the resistance of bacteria, but also make intestinal probiotics fail to survive, so that patients cannot be completely healed. Recent studies are devoted to developing fecal transplantation therapy, mainly involving transplanting feces of a healthy donor into the intestinal tract of a recipient to act against *Clostridium difficile* in the intestinal tract and improve the balance of intestinal flora in the recipient, thereby achieving the purpose of treating diseases such as diarrhea and acute enteritis.

The so-called metabolic syndrome is a collection of disease risk factors, including hypertension, pre-hypertension, dyslipidemia, diabetes, elevated blood glucose, obesity, hyperuricemia. Because the occurrence of risk factors is related to many chronic or metabolic diseases such as type 2 diabetes, cardiovascular disease, fatty liver, and obesity, metabolic syndrome is considered to increase the risk of the forgoing diseases. Statistically, the chance of developing heart disease in patients with metabolic syndrome is 2× higher than that in a common person. In addition, metabolic syndrome also may increase the risk of rapid deterioration of chronic or metabolic diseases.

Currently, no method capable of treating metabolic syndrome is presented clinically, and metabolic syndrome only can be improved by the change of an exercise habit and a diet habit. However, most people cannot maintain good lifestyle habits so that the control of metabolic syndrome is quite difficult.

SUMMARY OF THE INVENTION

A primary object of the present invention is to provide a method for treating and/or preventing metabolic syndrome and related diseases thereof, by administering a microbe composition to an individual to achieve the modulation of blood glucose, inhibition of body weight gain, reduction of low density cholesterol in blood, and reduction of hepatic expression of inflammatory factors, thereby effectively treating and/or preventing metabolic syndrome or related diseases thereof.

In one embodiment of the present invention, provided is a method for treating and/or preventing metabolic syndrome and related diseases thereof, including administering an effective amount of a composition to an individual such that the number of bacteria of genus AF12, genus *Helicobacter*, genus *Odoribacter*, or at least two genera of the foregoing in the gastrointestinal tract of the individual is increased.

Preferably, the composition includes at least one bacterium, and the bacterium belongs to genus AF12, genus *Helicobacter*, or genus *Odoribacter*. Further preferably, bacteria of genus AF12, genus *Helicobacter* and genus *Odoribacter* are included in the composition.

Preferably, the composition is prepared from feces, and the feces are derived from a donor having an exercise habit.

The definition of an exercise habit varies from one country to another. For example, it is specified by the Japanese Ministry of Ministry of Health, Labour, and Welfare (MHLW) that one having two exercises per week at above 30 min per exercise for above 1 year may be considered to have an exercise habit; it is considered by the Ministry of Education of R.O.C. (Taiwan) that one having three exercises per week at above 30 min per exercise can be regarded as having an exercise habit; and it is proposed in an exercise guideline published on 2008 in US that an exercise habit means moderate exercises for above 5 days per week at above 30 min per exercise, or a strenuous exercise for above 75 min per week. Therefore, the exercise habit in the present invention means an exercise frequency of 2 exercises per week at above 30 min per day, or an exercise at above 75 min per week.

Preferably, the donor has a non-high-fat diet habit, and the non-high-fat diet habit means that the proportion of fat in a daily diet is less than 77%.

Further, when the donor has both an exercise habit and a non-high-fat diet habit, the quality of feces is better.

Preferably, the disease related to metabolic syndrome is hyperlipidemia, cardiovascular disease, type 2 diabetes, obesity, fatty liver, hepatitis, or liver injury.

In another embodiment of the present invention, provided is a method for treating and/or preventing metabolic syndrome and related diseases thereof, including administering an effective amount of a composition to an individual, wherein the composition includes bacteria of at least one selected from genus AF12, genus *Helicobacter* and genus *Odoribacter*.

Preferably, the composition includes bacteria of genus AF12, genus *Helicobacter* and genus *Odoribacter*.

Preferably, the composition is prepared from feces, and the feces are derived from a donor having an exercise habit.

Preferably, the exercise habit means an exercise frequency of at least two exercises per week at above 30 min per exercise, or an exercise at above 75 min per week.

Preferably, the donor has a non-high-fat diet habit, and the non-high-fat diet habit means that the proportion of fat in a daily diet is less than 77%.

Further, when the donor has both an exercise habit and a non-high-fat diet habit, the quality of feces is better.

Preferably, the disease related to metabolic syndrome is hyperlipidemia, cardiovascular disease, type 2 diabetes, obesity, fatty liver, hepatitis, or liver injury.

In still another embodiment of the present invention, provided is a method for treating and/or preventing metabolic syndrome and related diseases thereof, including administering an effective amount of a composition to an individual, the composition being derived from feces of a donor, wherein the donor has at least one condition selected from the group consisting of an exercise habit and a non-high-fat diet habit.

Preferably, the exercise habit means an exercise frequency of at least two exercises per week at above 30 min per exercise, or an exercise at above 75 min per week.

Preferably, the non-high-fat diet means that the proportion of fat in a daily diet of the donor is less than 77%.

Preferably, the disease related to metabolic syndrome is hyperlipidemia, cardiovascular disease, type 2 diabetes, obesity, fatty liver, hepatitis, or liver injury.

Another object of the present invention is to provide a method for preparing a microbe composition, which is prepared from feces provided by a donor.

Specifically, in one embodiment of the present invention, provided is a method for preparing a microbe composition, including the following steps: a. taking feces from a donor; b. preparing the feces into a feces solution; and c. centrifuging and filtrating the feces solution to obtain a liquid microbe composition; wherein bacteria of genus AF12, genus *Helicobacter*, genus *Odoribacter*, or at least two genera of the foregoing are included in the feces.

Further, in the step b, the feces solution is prepared by mixing the feces with water and a NaCl solution. Specifically, the NaCl solution has a concentration of 0.9%.

Preferably, bacteria of genus AF12, genus *Helicobacter* and genus *Odoribacter* are included in the feces.

Preferably, the donor has an exercise habit and/or a non-high-fat diet habit, and more preferably, the donor has both an exercise habit and a non-high-fat diet habit.

Further, the exercise habit means an exercise frequency of at least two exercises per week at above 30 min per exercise, or an exercise at above 75 min per week; the non-high-fat diet means that the proportion of fat in a daily diet of the donor is less than 77%.

In another embodiment of the present invention, provided is a method for preparing a microbe composition, including the following steps: taking feces from a donor; preparing the feces into a feces solution; and centrifuging and filtrating the feces solution to obtain a liquid microbe composition; wherein the donor has at least one condition selected from the group consisting of an exercise habit and a non-high-fat diet habit.

Further, in the step b, the feces solution is prepared by mixing the feces with water and a NaCl solution. Specifically, the NaCl solution has a concentration of 0.9%.

Preferably, the exercise habit means an exercise frequency of at least two exercises per week at above 30 min per exercise, or an exercise at above 75 min per week.

Preferably, the non-high-fat diet means that the proportion of fat in a daily diet of the donor is less than 77%.

A further object of the present invention is to provide a method for detecting the health condition and predicting the risk in an individual, by using bacteria in the gastrointestinal tract as biomarkers to achieve the prediction or identification of the health risk of the individual.

In one embodiment of the present invention, provided is a method for identifying the risk of body weight gain in an individual, including detecting bacteria in the gastrointestinal tract of the individual, wherein the bacteria are selected from genus AF12, genus *Helicobacter*, genus *Odoribacter*, or at least two genera of the foregoing.

In another embodiment of the present invention, provided is a method for predicting the risk of developing metabolic syndrome and related diseases thereof in an individual, including detecting bacteria in the gastrointestinal tract of the individual, wherein the bacteria are selected from genus AF12, genus *Helicobacter*, genus *Odoribacter*, or at least two genera of the foregoing.

Preferably, the disease related to metabolic syndrome is hyperlipidemia, cardiovascular disease, type 2 diabetes, obesity, fatty liver, or hepatitis.

A still another object of the present invention is to provide a method for reducing body weight, by administering an effective amount of a microbe composition to an obese individual to achieve the reduction in body weight.

In one embodiment of the present invention, provided is a method for reducing body weight, including administering an effective amount of a composition to an individual such that the number of bacteria of genus AF12, genus *Helicobacter*, genus *Odoribacter*, or at least two genera of the foregoing in the gastrointestinal tract of the individual is increased.

Preferably, the composition includes bacteria of genus AF12, genus *Helicobacter* and genus *Odoribacter*.

In another embodiment of the present invention, provided is a method for reducing body weight, including administering an effective amount of a composition to an individual, the composition being derived from feces of a donor, wherein the donor has at least one condition selected from the group consisting of an exercise habit and a non-high-fat diet habit.

Preferably, the exercise habit means an exercise frequency of at least two exercises per week at above 30 min per exercise, or an exercise at above 75 min per week.

Preferably, the non-high-fat diet means that the proportion of fat in a daily diet of the donor is less than 77%.

DETAILED DESCRIPTION OF THE PREFERRED EMBODIMENTS

The present invention is further described below with several examples in connection with the drawings.

A donor in the present invention refers to an individual providing feces, and a donor and a recipient are not defined as different individuals.

A non-high-fat diet in the present invention means that the proportion of fat in a daily diet is less than 77%, such as 70%, 60%, 50%, 40%, 30%, which is obtained by conversion from the experimental results in animals. For example, a high-fat animal model used in the present invention is established by administering a 60 kcal % diet, and it can be obtained after conversion that the proportion of fat in the diet is 77%.

An exercise habit in the present invention means that an individual adheres to an exercise program, with an exercise frequency of at least 2 exercises per week at above 30 min per exercise, or an exercise at above 75 min per week.

A recipient in the present invention refers to an individual receiving a microbe composition in the present invention.

A microbe composition in the present invention is one which can be prepared from feces provided by a donor, or a composition made by the common knowledge in the art to which the present invention belongs or the commercial process known at present, and includes bacteria of genus AF12, genus *Helicobacter*, genus *Odoribacter*, or at least two genera of the foregoing.

Further, a microbe composition in the present invention may be prepared into a formulation, such as powder, capsule, tablet, liquid, or gel, which can be administered to a recipient, and suitable food acceptable or pharmaceutically acceptable excipients and carriers may be selected depending on the formulation.

Metabolic syndrome in the present invention refers to a cluster of metabolic risk factors, including risk factors such as hypertension, hyperlipidemia, obesity, hyperglycemia, elevated blood triglycerides, elevated fasting blood glucose, and impaired glucose tolerance.

The animal experiments and procedures thereof in the following examples are approved by the local IACUC (La-1031216, La-1041342).

Example 1: Animal Experiment

Figure 1:
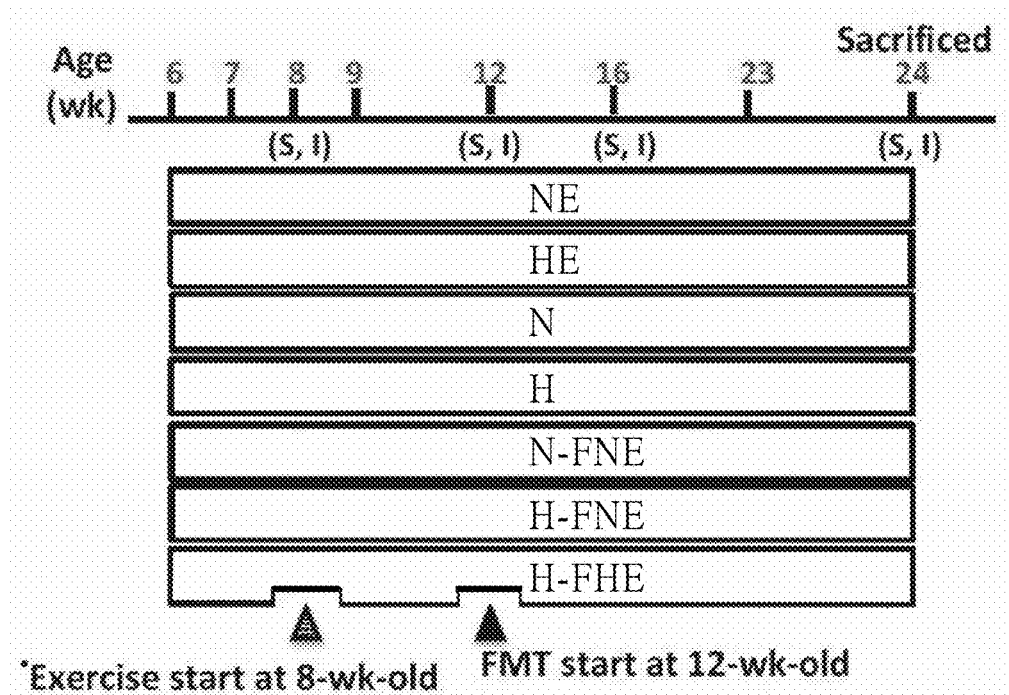
FIG. 1 is a schematic view of the design of experiments.

Five-week-old mice were obtained from Taiwan National Laboratory Animal Center. Refer to FIG. 1. The mice were randomly divided into seven groups, housed in an environment at a controlled temperature of 22±1° C. and under a 12 h light cycle (with an illumination period of from 8 p.m. to 8 a.m.) until they were sacrificed at 24-week old, as follows:

group N: normal diet;
group NE: normal diet and exercise;
group N_FNE: normal diet and fed with a transplantation composition from group NE;
group H: high-fat diet;
group HE: high-fat diet and exercise;
group H_FHE: high-fat diet and fed with a transplantation composition from group HE;
group H_FNE: high-fat diet and fed with a transplantation composition from group NE.

A normal diet group was given with a normal diet (Fwusow Industry, Taichung, Taiwan) and water; a high-fat diet group was given with a high-fat diet (HFD, Research Diets, USA) and water.

For an exercise group, mice were trained on a running machine (TREADMILL EXERCISER, Model T603, Singa, Diagnostic & Research Instruments Co., Ltd., Taoyuan, Taiwan) from 8-week old, and those mice rejecting the training after five pushes or weighing less than 21 g were excluded. Mice should be acclimated at two days per week, such that they were familiar with the running machine, without undue exercises. After the acclimation training, training on the running machine was initiated, starting at a speed of 7 m/min for warm-up for 5 min, followed by an acceleration of 3 m/min$^2$ to a speed of 18 m/min for 30 min. The training frequency was 5 days per week.

A group fed with a transplantation composition was housed to 12-week old, and then administered with a transplantation composition daily in a dosage of 100 μL per mouse for a total feeding period of 3 months, and antibiotics Ciprofloxacin (0.2 g/L) and Metronidazole (1 g/L) (Sigma-Aldrich Corp., MO, USA) were given two days before administering feces.

Example 2: Preparation of a Feces Composition

For groups NE and HE of mice, after 4 weeks of exercise training (i.e., 12-week old), their feces were collected daily, and a transplantation composition was prepared within 10 min before groups N_FNE, H_FHE and H_FNE were gavage-fed daily, as follows.

About 100 mg of feces were collected from groups NE and HE of mice respectively, suspended in 1 mL of a sterile saline solution, mixed to form a microbe solution, and centrifuged at 800 g for 3 min, and the supernatant (about 500-600 μL) was collected and filtrated with a 70 mm screen to give a filtrate, i.e. a transplantation composition.

Example 3: Changes in Body Weight and Fat

Figure 2:
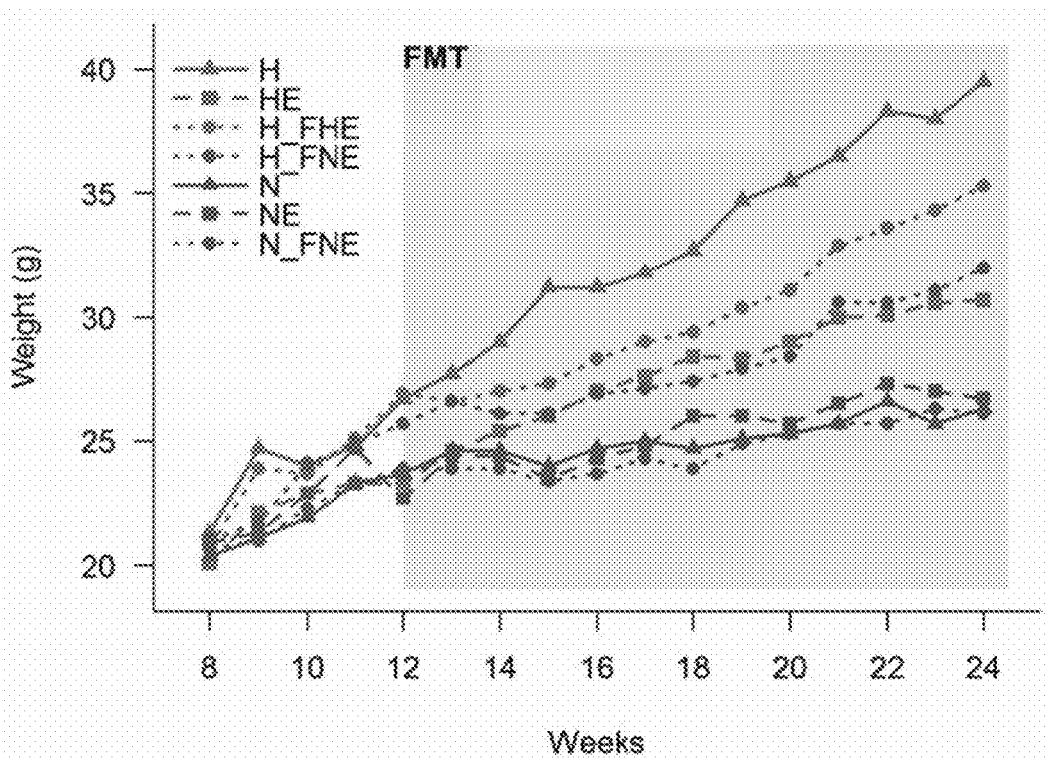
FIG. 2 is the change in body weight of each group of mice.

The body weight of each group of mice was measured weekly, as shown in FIG. 2. During and after the experiments, the fat mass of each group of mice was measured, as shown in FIG. 3.

Figure 3:
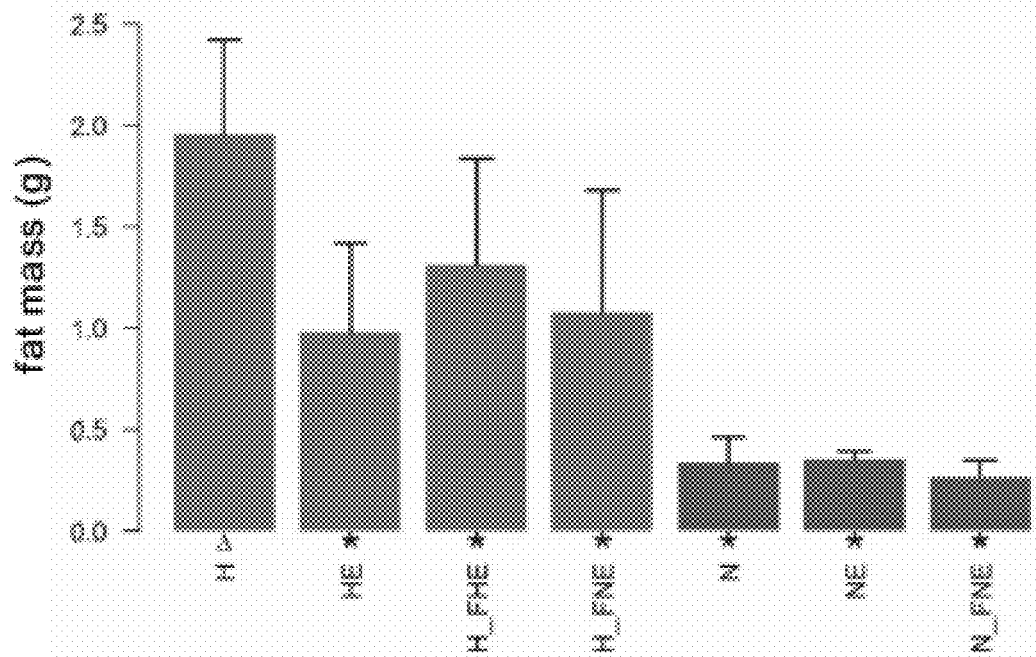
FIG. 3 is the fat mass of each group of mice.

It can be known from FIG. 2 and FIG. 3 that by comparing the body weight of groups N, NE and N_FNE fed with the normal diet, despite no exercise in group N_FNE, feeding with the transplantation composition prepared from feces in group NE results in no difference in body weight and fat mass between group N_FNE and groups NE and N.

From the body weight and fat mass of each group fed with the high-fat diet, although feeding with the high-fat diet indeed leads to significant increase in body weight and fat mass of an individual, if the individual has a constant exercise habit or fed with a transplantation composition from an individual having an exercise habit, both body weight and fat mass of the recipient can be significantly reduced, and when the transplantation composition is derived from a donor having a normal diet and an exercise habit, the decrease in body weight of the recipient is close to that of one having a high-fat diet and having an exercise habit.

As can be seen, when the source of a transplantation composition is a donor having an exercise habit, the transplantation composition can effectively reduce the body weight and fat mass of an individual, and when the diet of the donor is not a high-fat diet, the effect of controlling the body weight and fat mass of the recipient is equivalent to that of one having an exercise habit. In other words, a transplantation composition from a donor having an exercise habit can be used for treating and/or preventing obesity and related diseases thereof.

Example 4: Measurement of Blood Glucose Value

Figure 4:
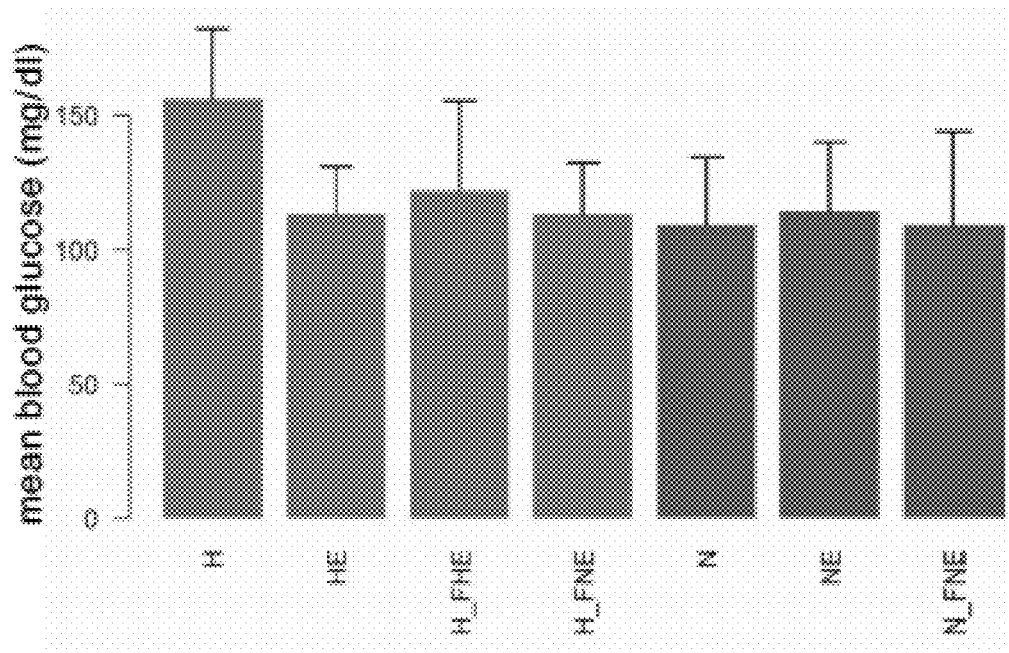
FIG. 4 is the mean blood glucose of each group of mice.
Figure 5:
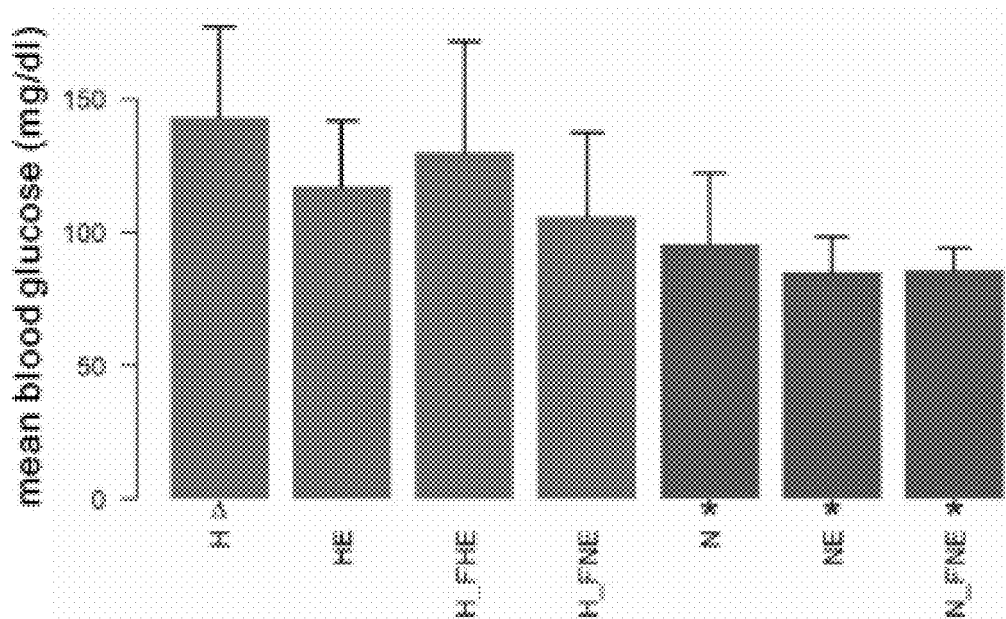
FIG. 5 is the mean blood glucose at 24 weeks of each group of mice.
Figure 6:
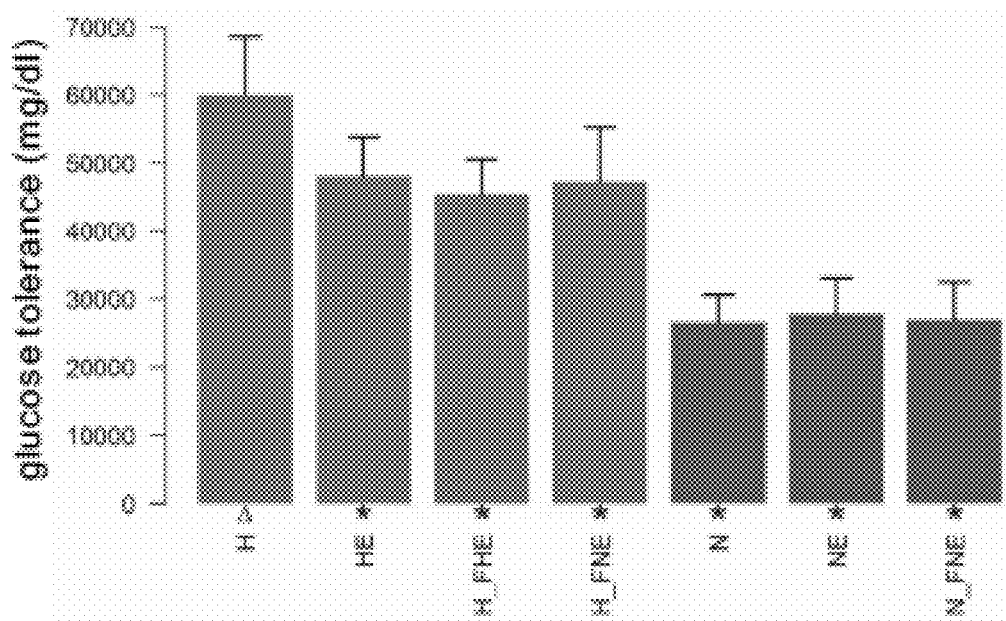
FIG. 6 is the glucose tolerance measured at week 24 of each group of mice, which is a mean of area under the blood glucose-time curve.

The fasting blood glucose of each group of mice was measured weekly and at 24-week old, and IPGTT (Intraperitoneal Glucose Tolerance Test) was performed at 8-, 12-, 16-, and 24-week old for each group of mice, as shown in FIG. 4 to FIG. 6. The detection method of IPGTT was as follows: after 16 h fasting, 20% glucose and normal saline (2 g glucose/kg body mass) were intraperitoneally injected into each group of mice, and blood glucose was measured at 0, 30, 60, 90, and 120 min using GM700 (BIONIME, Taichung, Taiwan).

It can be known from the results in FIG. 4 to FIG. 6 that on the basis of feeding with a normal diet, with exercises or no exercises, administering a transplantation composition from an exercise group leads to maintenance in blood glucose and glucose resistance of an individual. When mice were fed with a high-fat diet, blood glucose and glucose resistance of the mice can be significantly increased compared to those in mice having a normal diet. However, when the mice have an exercise habit or fed with a transplantation composition from a donor having an exercise habit, both blood glucose and glucose resistance of the mice can be relatively close to those in the blank group, and the effect is better when the transplantation composition is derived from a donor having both an exercise habit and a normal diet.

Accordingly, a transplantation composition from a donor having an exercise habit can effectively treat and/or prevent diseases related to blood glucose regulation, for example, type 2 diabetes.

Example 5: Detection of LDL in Blood

Figure 7:
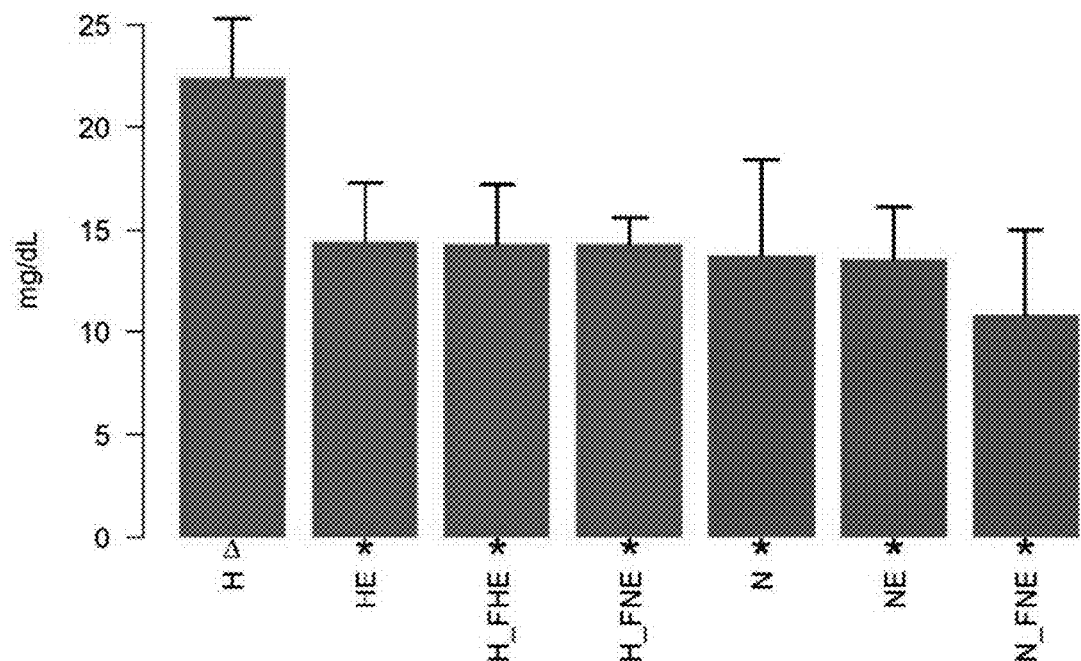
FIG. 7 is the level of low density cholesterol in blood of each group of mice.
Figure 8:
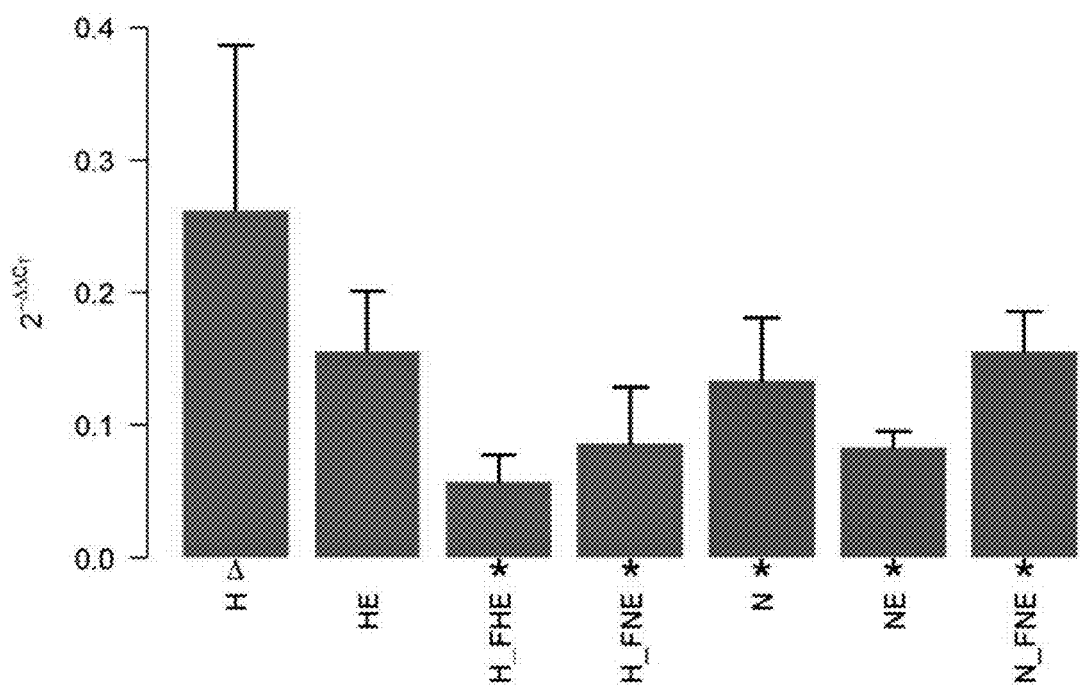
FIG. 8 is the expression amount of TNF-α in liver of each group of mice.
Figure 9:
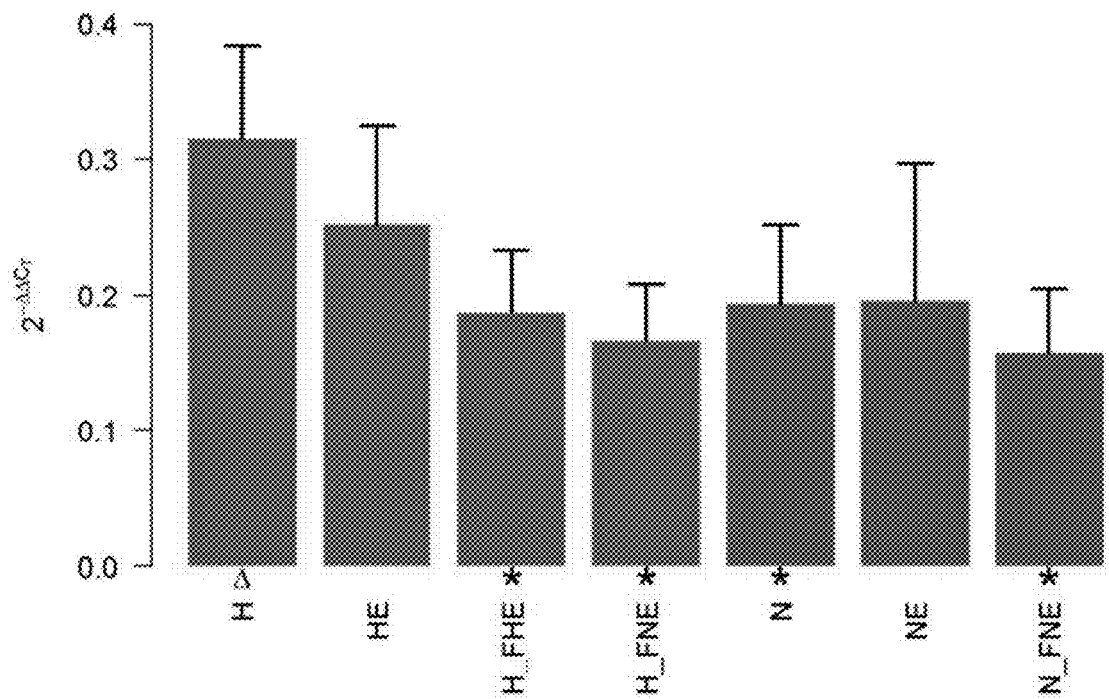
FIG. 9 is the expression amount of 1 L-1α in liver of each group of mice.
Figure 10:
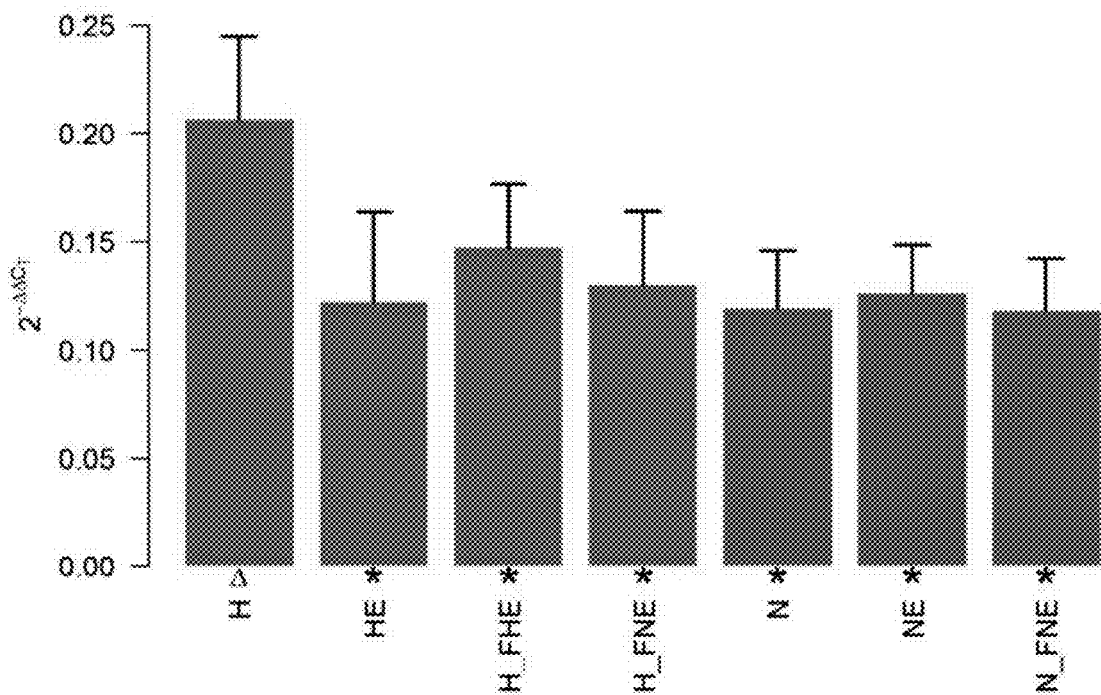
FIG. 10 is the expression amount of PPAR-γ in liver of each group of mice.
Figure 11:
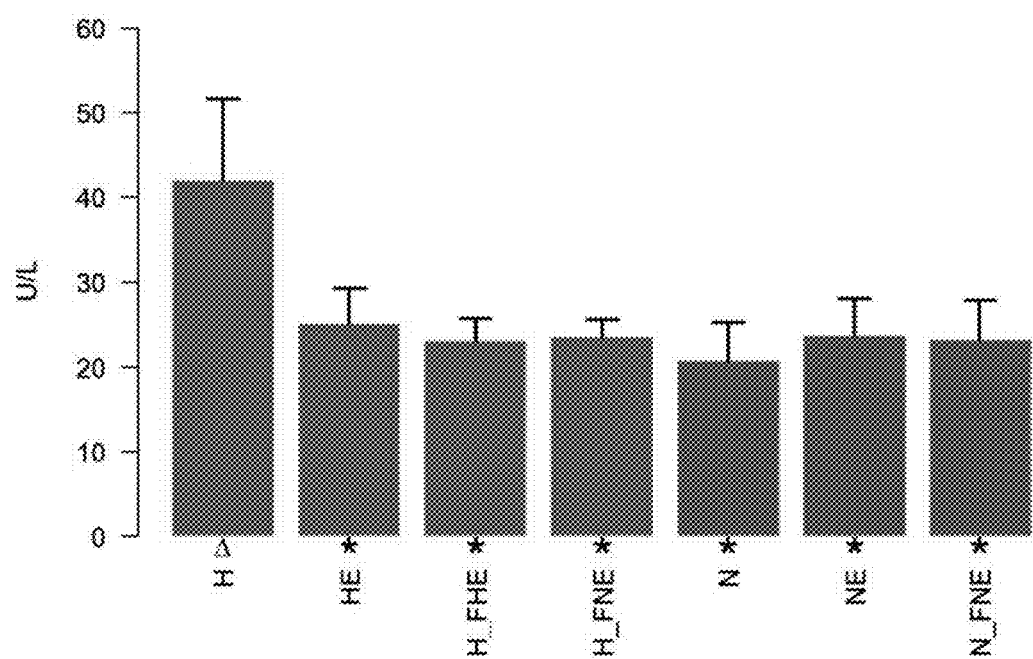
FIG. 11 is the expression amount of ALT in liver of each group of mice.

After each group of mice were sacrificed, about 0.1-1 mL blood was taken from their heart respectively, serum and blood cells were isolated by centrifugation at 3000 g at 4° C., and the level of LDL in serum was measured, as shown in FIG. 7.

It can be known from the results in FIG. 7 that a high-fat diet can make low density cholesterol in blood of an individual significantly higher than that of one having a normal diet, but with an exercise habit or administering a transplantation composition from a donor having an exercise habit, the level of low density cholesterol in blood of a recipient having a high-fat diet can be effectively reduced. Furthermore, with a normal diet, if a transplantation composition from a donor having an exercise habit is administered, the level of low density cholesterol in blood of a recipient can also be effectively reduced.

As can be seen, a transplantation composition from a donor having an exercise habit has the effect of reducing the level of low density cholesterol, and thus can be used for treating and/or preventing metabolic syndrome and related diseases thereof.

Example 6: Detection of Protein Expression in Hepatic Tissue

The liver tissue of each group of mice was taken, and after protein extraction, the expression of TNF-α, 1L-1α, PPAR-γ, and ALT in liver was detected. The techniques of protein extraction and detection of protein expression are the common knowledge in the art to which the present invention belongs and thus not repeatedly described herein. The detection results are shown in FIG. 8 to FIG. 11.

It can be known from the results in FIG. 8 to FIG. 11 that feeding with a high-fat diet may result in an inflammatory condition of mouse liver, and thus the measured amounts of expression of inflammation related factors TNF-α, 1L-1α, PPAR-γ, and ALT all are significantly higher than those in the blank group fed with a normal diet. Feeding with a high-fat diet followed by administering a transplantation composition from a donor having an exercise habit can significantly reduce the amounts of expression of inflammation related factors in liver, and when the donor of the transplantation composition has both an exercise habit and a non-high-fat diet habit, the transplantation composition can more effectively reduce the amounts of expression of inflammation related factors.

As can be seen, a transplantation composition from a donor having an exercise habit has the effect of reducing the liver inflammation index, and thus can be used for treating and/or preventing liver inflammation, liver fibrosis, fatty liver, and other liver inflammation related diseases.

Example 7: Pretreatment of Feces Samples

Feces of each group of mice were collected at 8-, 12-, 16-, and 24-week old, and quickly frozen for storage in a refrigerator at −80° C., and the delivery time was no more than 24 h.

Bacterial gDNA was extracted from the feces of each group of mice with Qiagen DNA isolation kit (Qiagene, MD, USA). For example, about 15-20 μg of gDNA could be produced from about 20 mg of a feces sample. The bacterial gDNA extracted from the feces of each group of mice could be used for real-time PCR quantitative analysis and 16S rRNA gene sequencing, where concentration detection and quantification of gDNA were performed with NanoDrop ND-1000 (Thermo Scientific, Wilmington, Del., USA), and gDNA at a concentration of 500 ng and 250 ng could be used for 16S rRNA gene sequencing and real-time PCR detection respectively.

Example 8: 16S rRNA Gene Sequencing and Analysis

The hypervariable region V3-V4 of bacterial 16S rRNA genes was PCR-amplified, using barcoded universal primers 341F: SEQ ID No.: 1 and 805R: SEQ ID No.: 2. The sequencing of the amplified DNA and library construction were completed by Genomics BioScience (Taipei, Taiwan). A pair-end library was constructed by using MiSeq Reagent Kit v3 (Illumina, Wilmington, Del., USA) (insertion size of 465 bp for each sample), and high-throughput sequencing was performed on Illumina MiSeq 2000 platform (Illumina).

16S rRNA bioinformatics analysis was performed by merging end reads of each sample using USEARCH (v7.0.1090), with minimum overlap in read base pairs set at 8 base pairs. Merged reads were quality-filtered with Mothur (v1.34.3) to remove reads shorter than 450 bp or longer than 550 bp, with reads having minimum average quality score <27. In addition, reads containing an ambiguous base or homopolymer exceeding 8 bp were excluded. The chimera detection was performed using USEARCH (reference mode and 3% minimum divergence).

Quality-filtered and non-chimeric reads were analyzed (UPARSE pipeline) to generate OTUs (operational taxonomic units) per sample (at 97% identify level). The OTU representative sequences were searched against the Greengenes 13_5 database using USEARCH global alignment to identify the corresponding taxonomy of the best hit. Any OTU without a hit or with only a weak hit, i.e. the function "(% sequence identity+alignment coverage)/2" was <93, was excluded from further analysis. The abundance of each taxon was counted and corrected with PICRUST, in which the pipeline divided the read count of each taxon by the corresponding 16S rRNA gene copy number. Diversity indices, e.g., Shannon, Simpson, Chao 1, and Good's coverage, were estimated with Mothur.

Example 9: Microbiota Analysis

Figure 12:
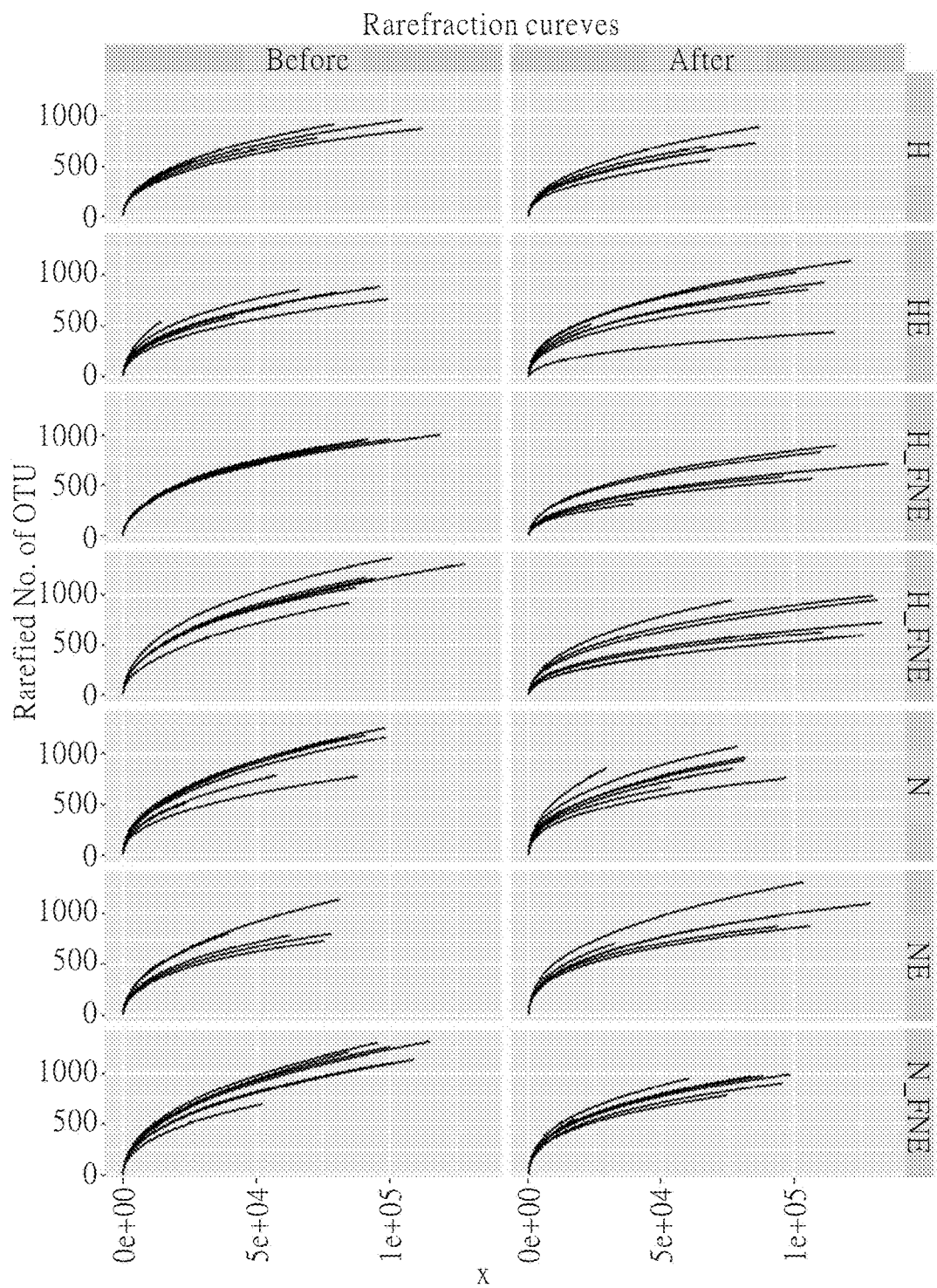
FIG. 12 is the analysis results of taxonomic units of the gastrointestinal microbiota in each group of mice.
Figure 13:
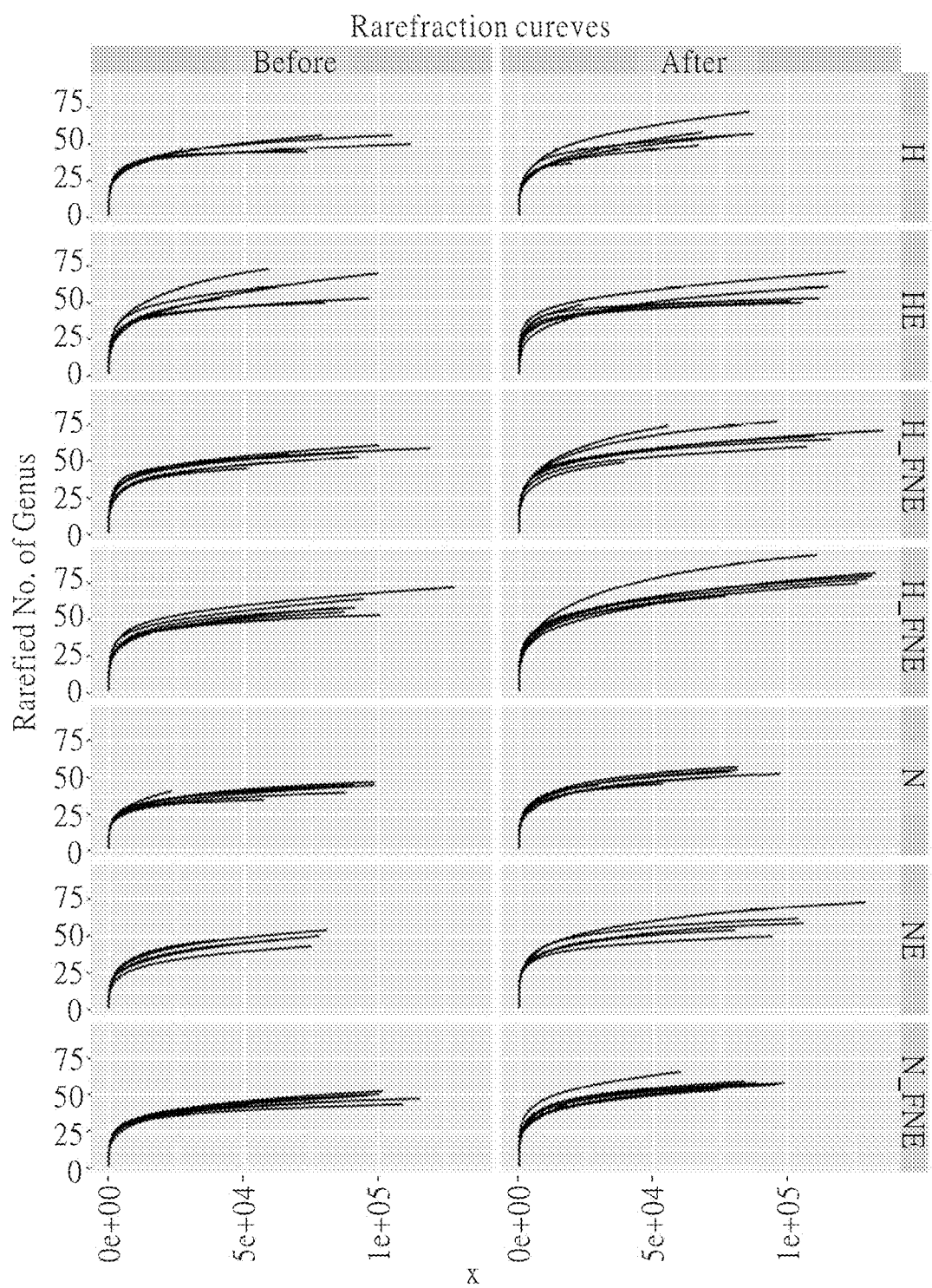
FIG. 13 is the analysis results of genera of the gastrointestinal microbiota in each group of mice.
Figure 14A:
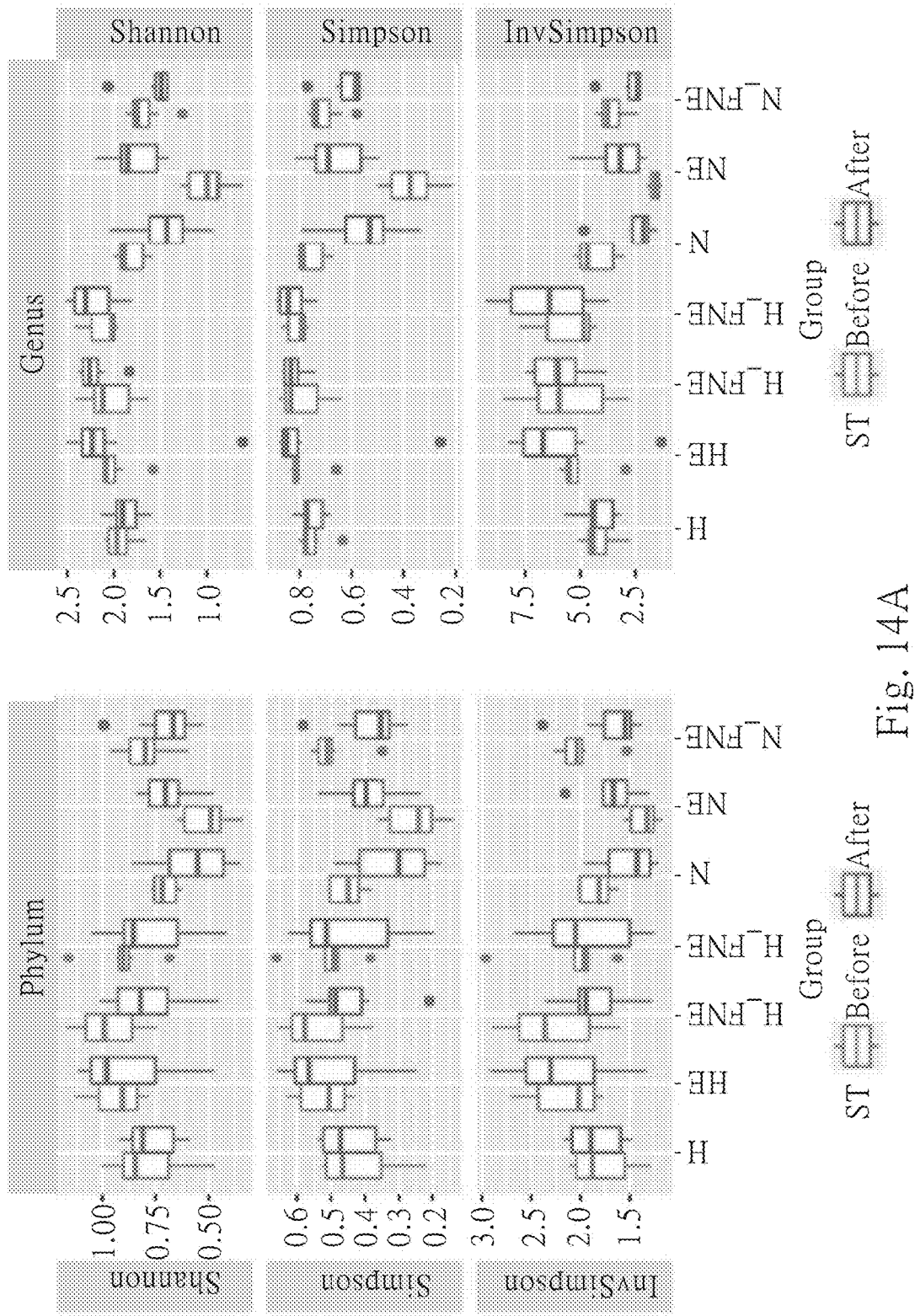
FIG. 14A is the analysis results of diversity index of the gastrointestinal microbiota in each group of mice.
Figure 14B:
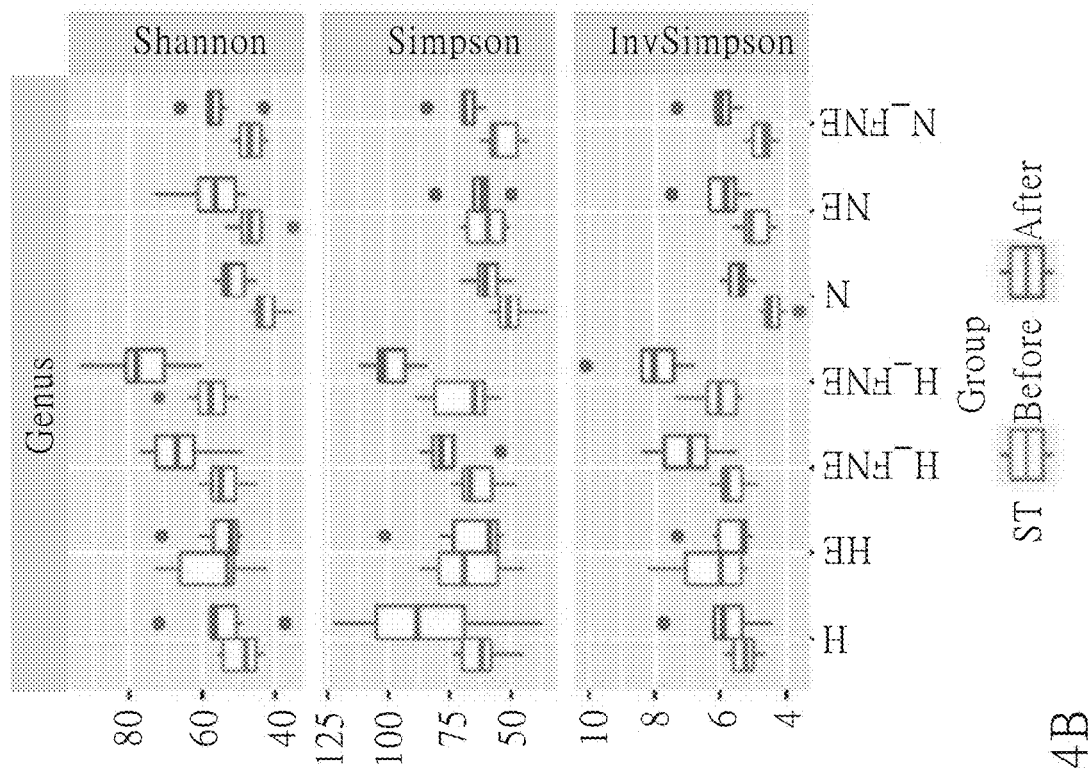
FIG. 14B is the analysis results of diversity index of the gastrointestinal microbiota in each group of mice.
Figure 14B:
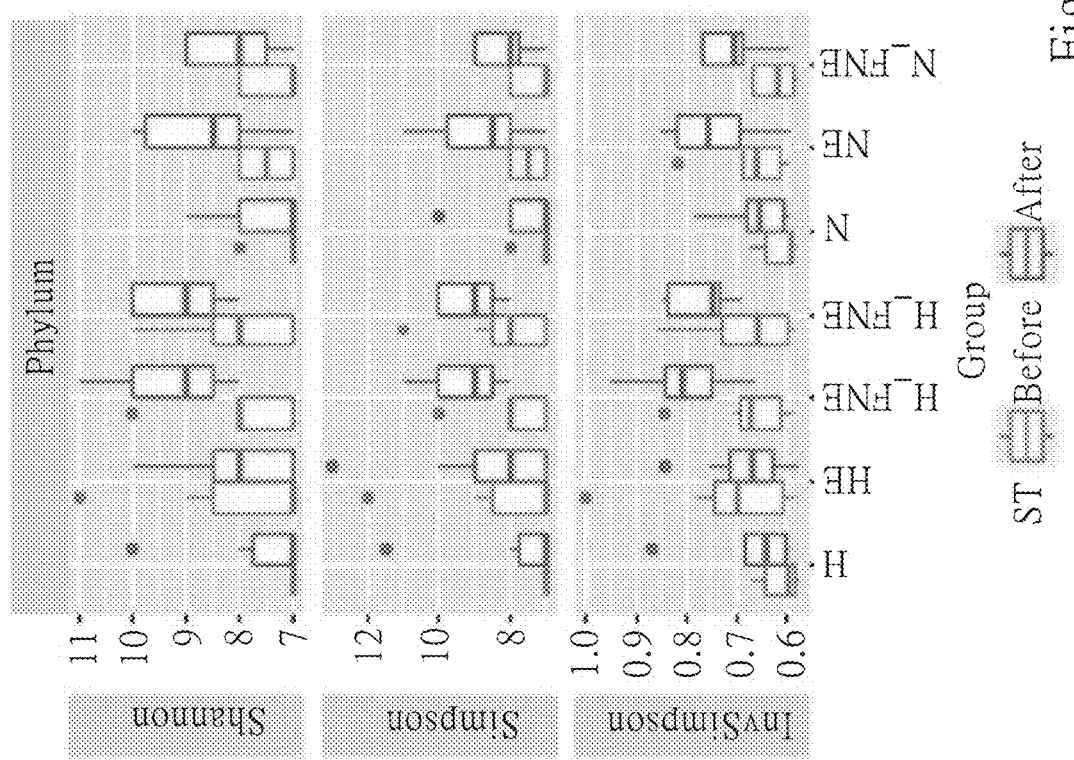

It can be known from FIG. 12 to FIG. 14 that the gastrointestinal microbiota in each group of mice all vary due to different housing conditions, and it can be known from the dilution curves of each group of mice that the diversity of microbiota is increased compared to that before taking exercises or administering a transplantation composition. In other words, the change in lifestyle habits such as a diet habit or an exercise habit can result in the change in flora distribution and composition of the gastrointestinal microbiota in a recipient.

Figure 15:
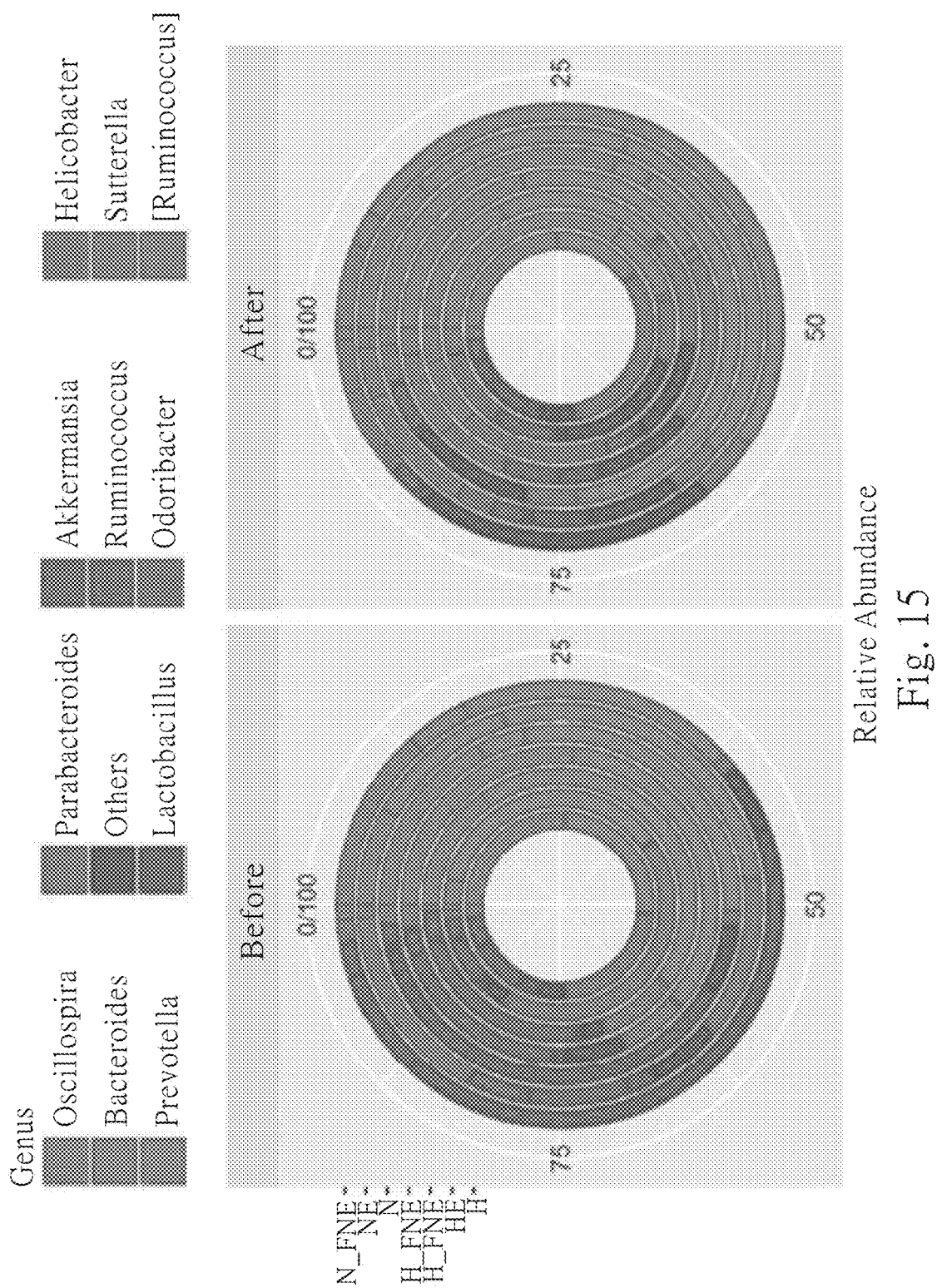
FIG. 15 shows the change in the gastrointestinal microbiota before and after the experiments of each group of mice.
Figure 16:
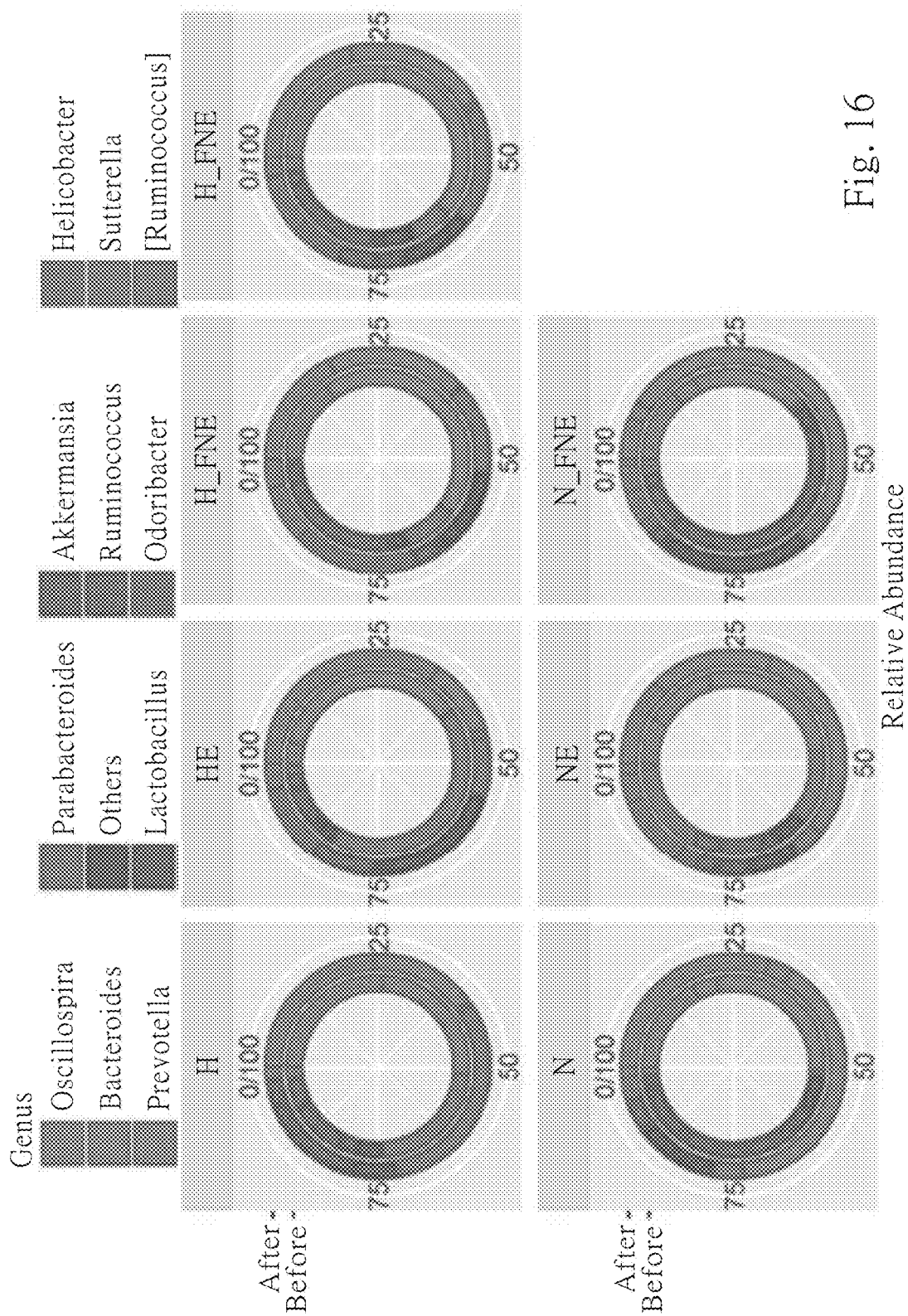
FIG. 16 shows the change in the gastrointestinal microbiota before and after the experiments of each group of mice.
Figure 17:
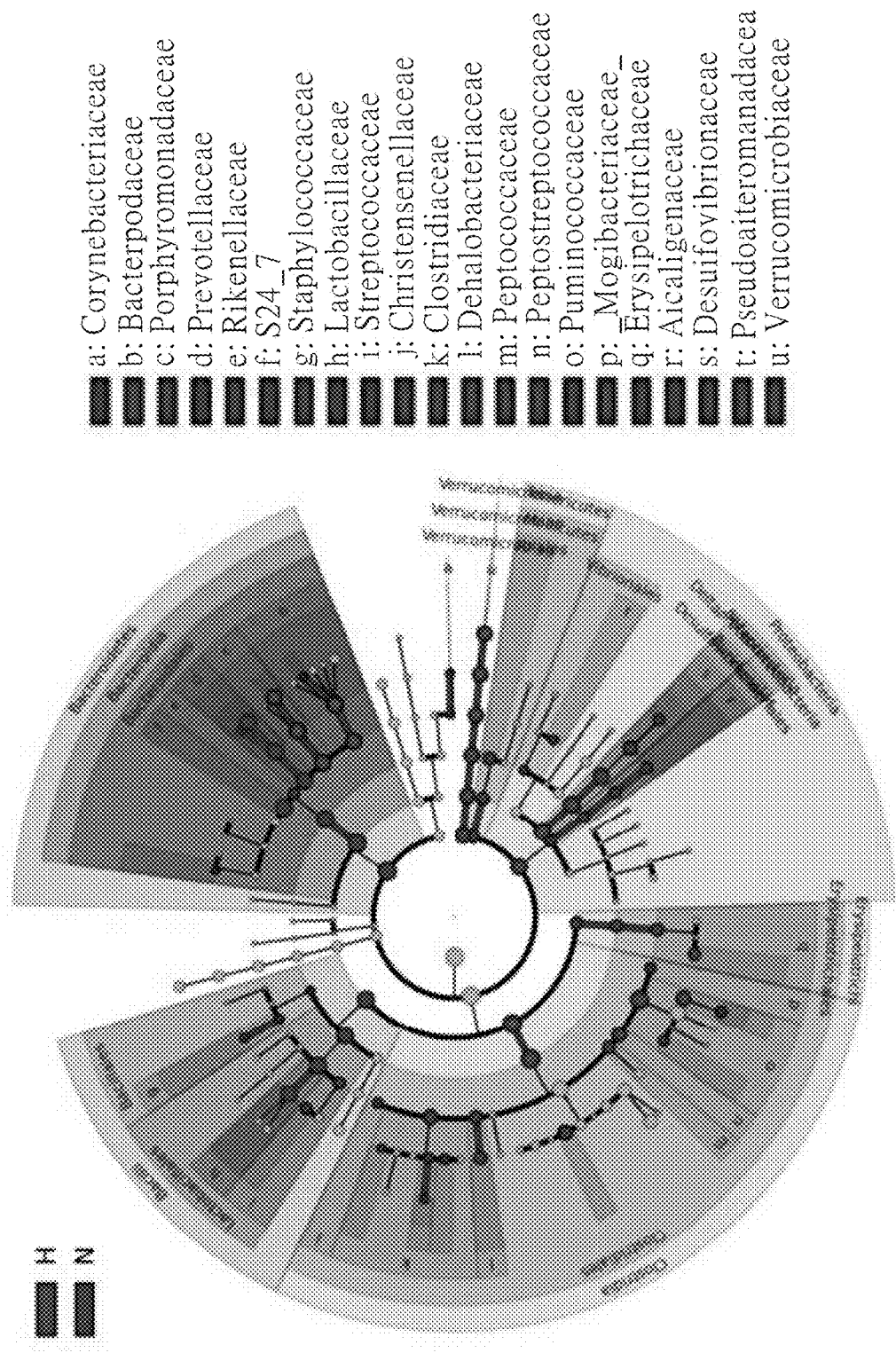
FIG. 17 shows the results of the gastrointestinal microbiota before the experiments of group H and group N of mice by the LefSe analysis.
Figure 18:
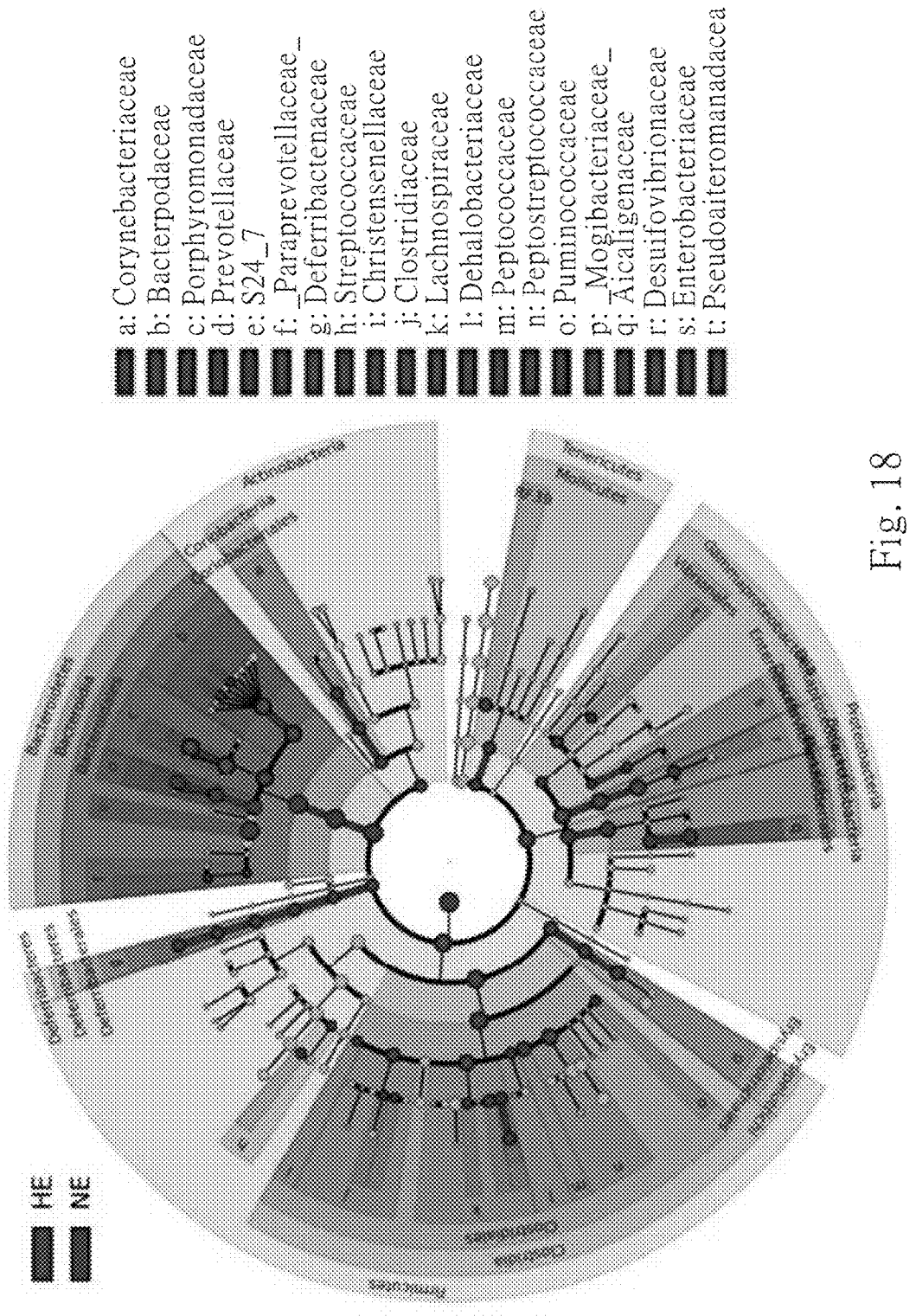
FIG. 18 shows the results of the gastrointestinal microbiota before the experiments of group HE and group NE of mice by the LefSe analysis.
Figure 19:
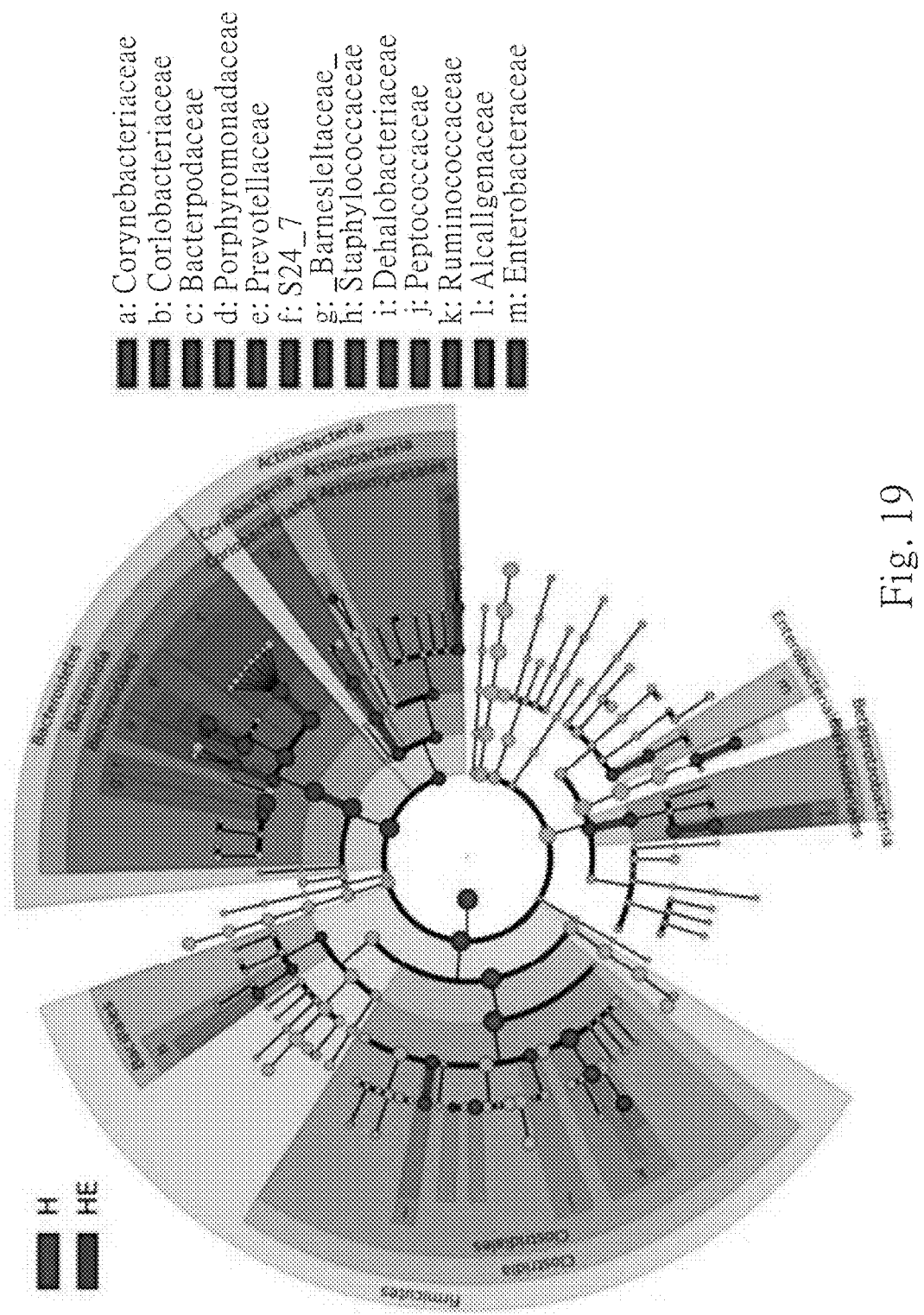
FIG. 19 shows the results of the gastrointestinal microbiota before the experiments of group H and group HE of mice by the LefSe analysis.
Figure 20:
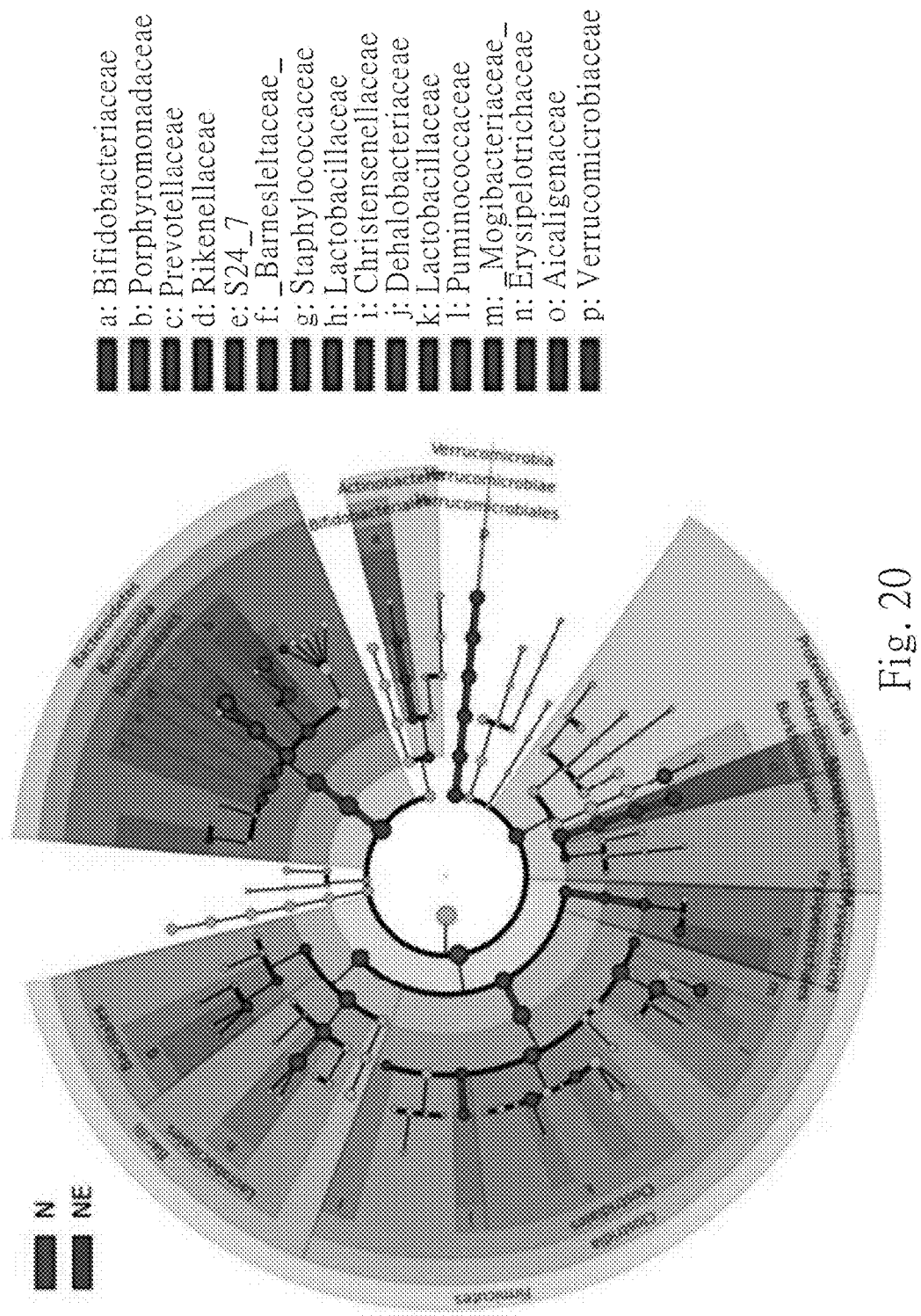
FIG. 20 shows the results of the gastrointestinal microbiota before the experiments of group N and group NE of mice by the LefSe analysis.
Figure 21:
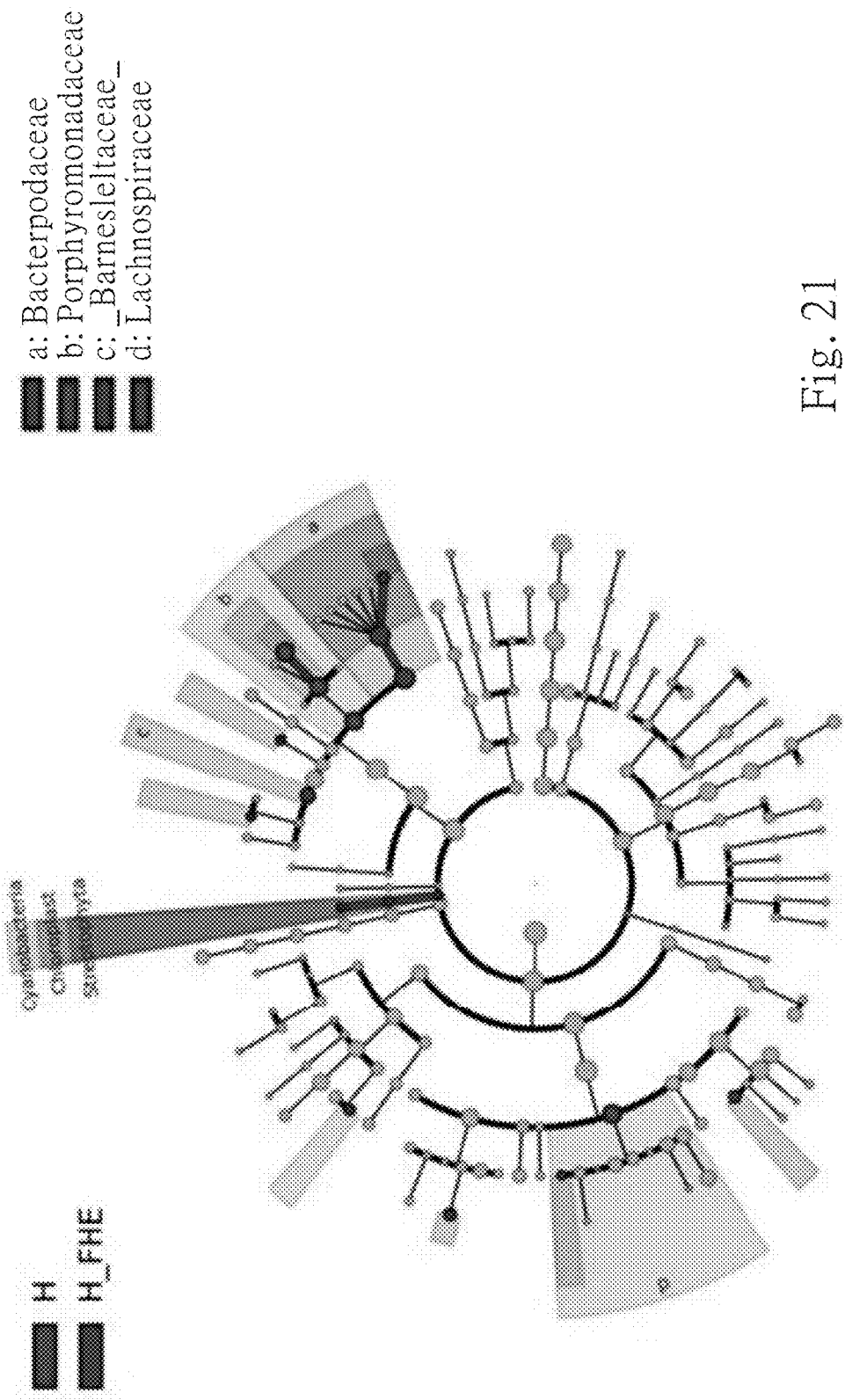
FIG. 21 shows the results of the gastrointestinal microbiota before the experiments of group H and group H_FHE of mice by the LefSe analysis.
Figure 22:
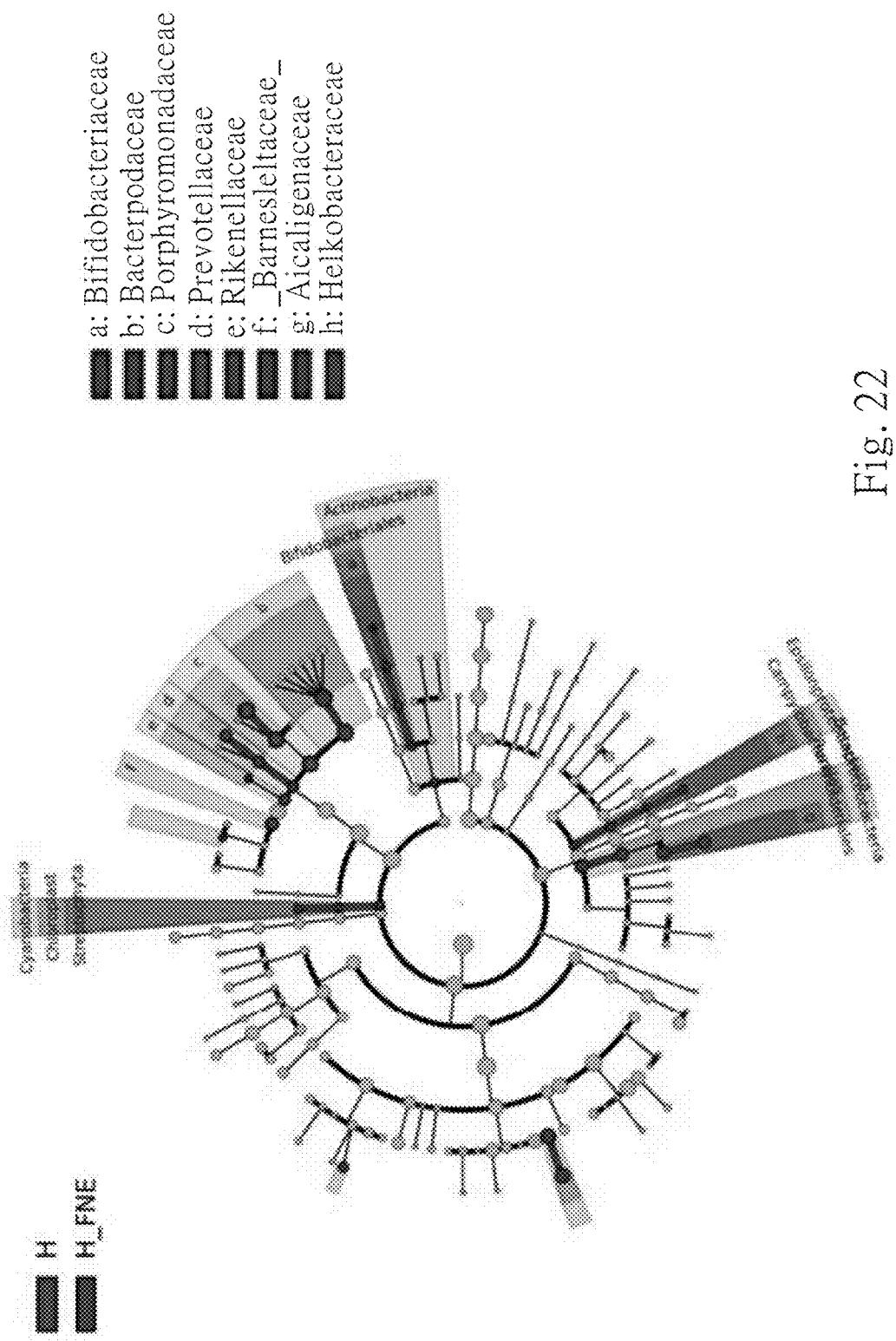
FIG. 22 shows the results of the gastrointestinal microbiota before the experiments of group H and group H_FNE of mice by the LefSe analysis.
Figure 23:
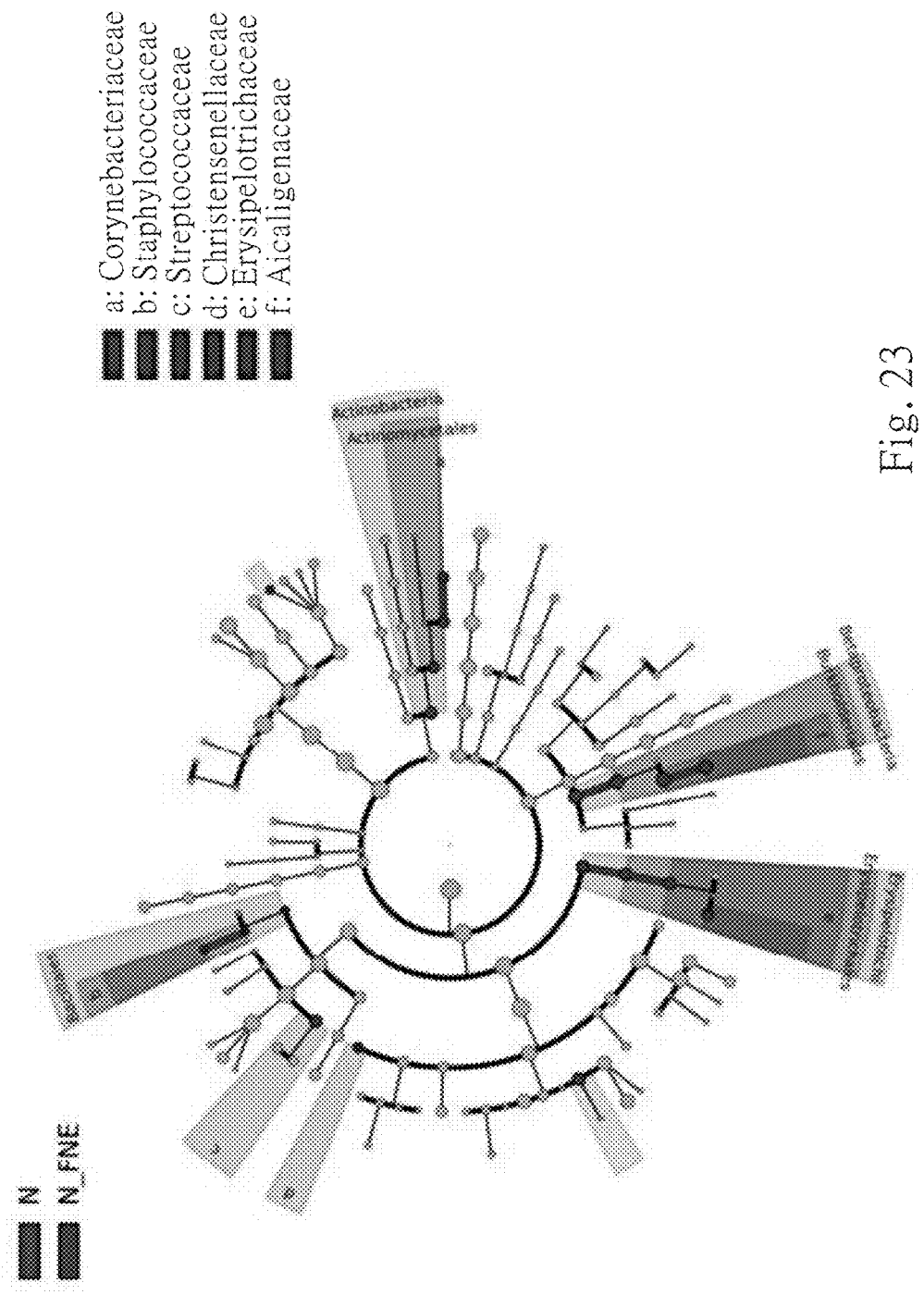
FIG. 23 shows the results of the gastrointestinal microbiota before the experiments of group N and group N_FNE of mice by the LefSe analysis.
Figure 24:
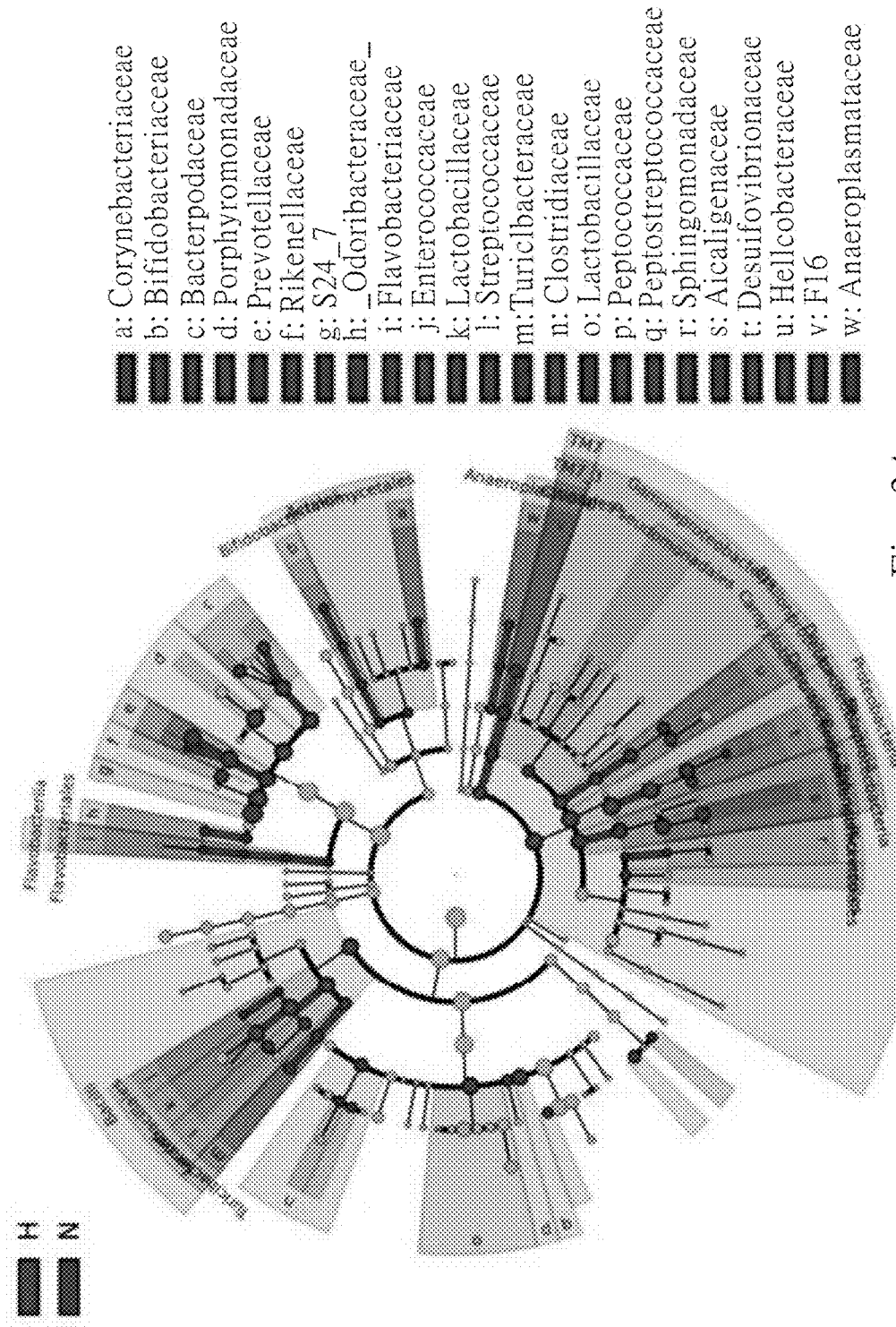
FIG. 24 shows the results of the gastrointestinal microbiota after the experiments of group H and group N of mice by the LefSe analysis.
Figure 25:
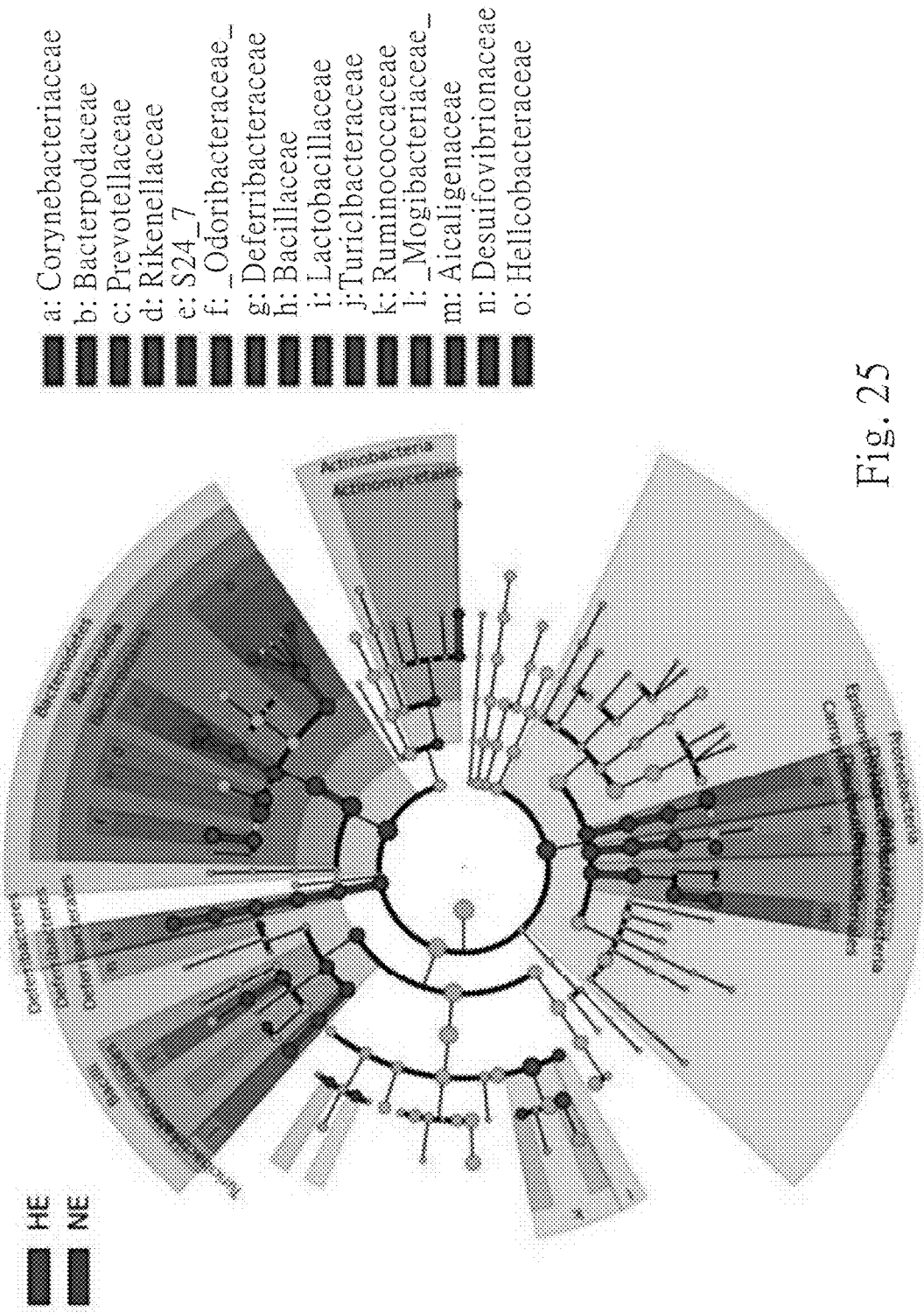
FIG. 25 shows the results of the gastrointestinal microbiota after the experiments of group HE and group NE of mice by the LefSe analysis.
Figure 26:
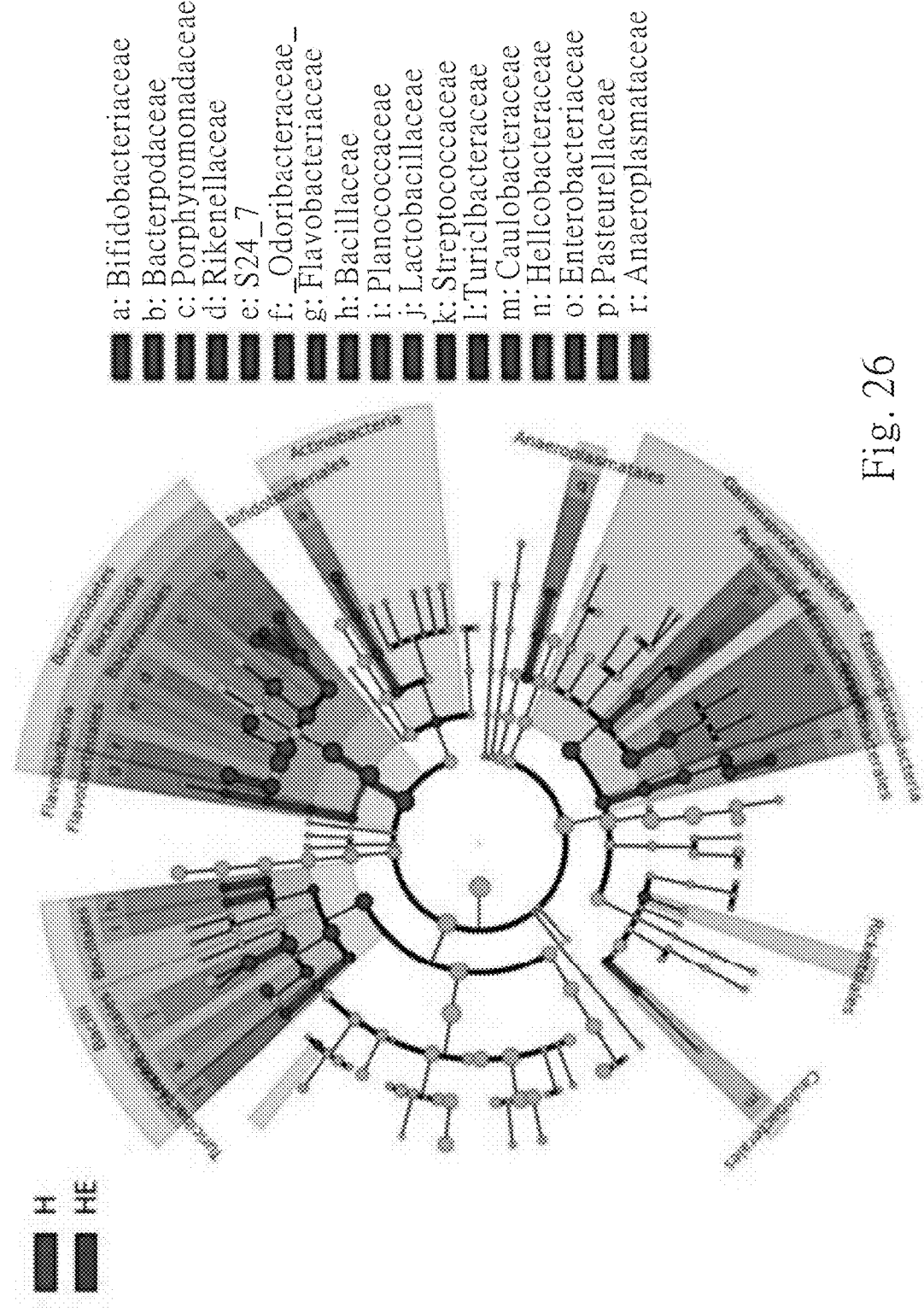
FIG. 26 shows the results of the gastrointestinal microbiota after the experiments of group H and group HE of mice by the LefSe analysis.
Figure 27:
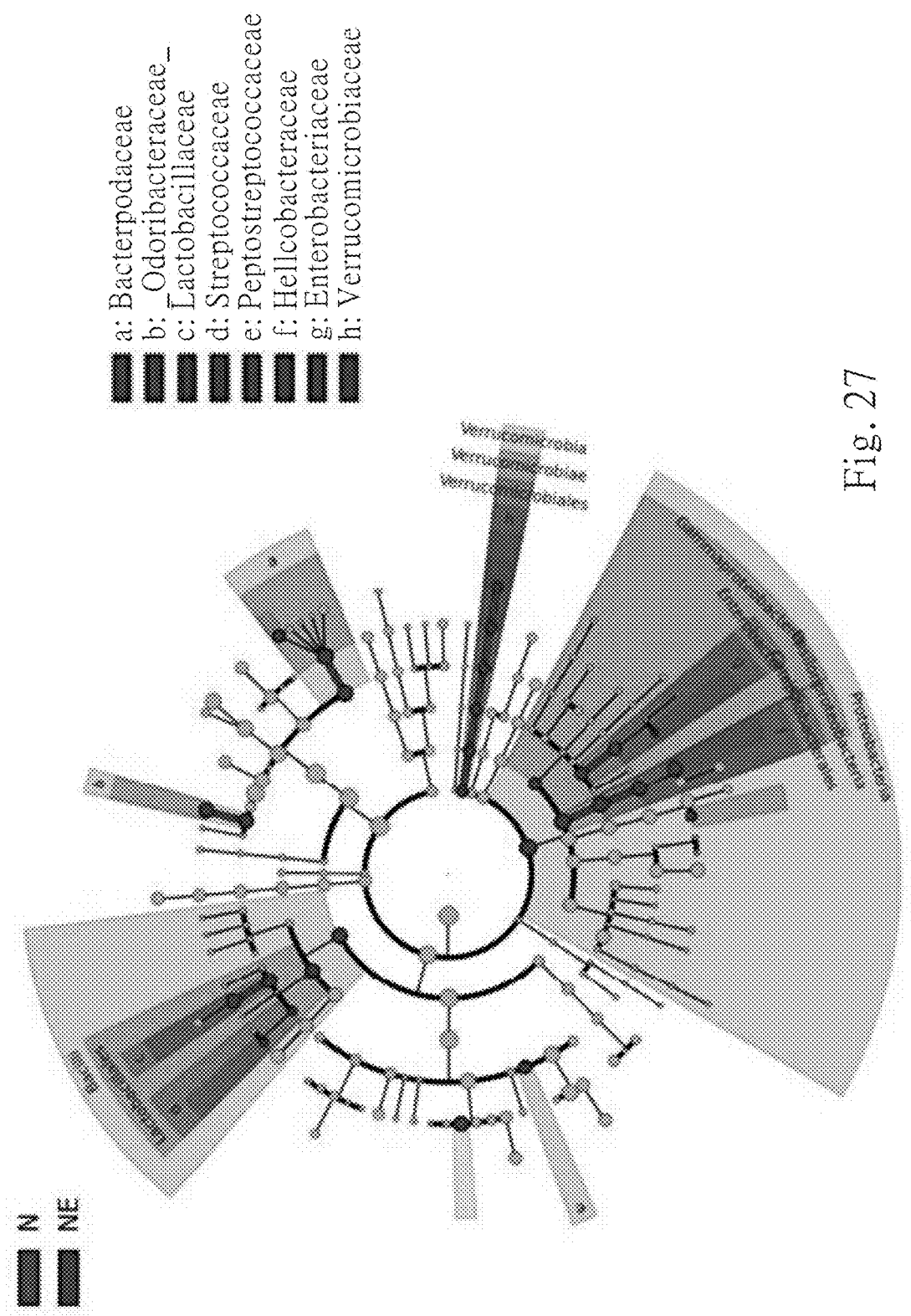
FIG. 27 shows the results of the gastrointestinal microbiota before and after the experiments of group N and group NE of mice by the LefSe analysis.
Figure 28:
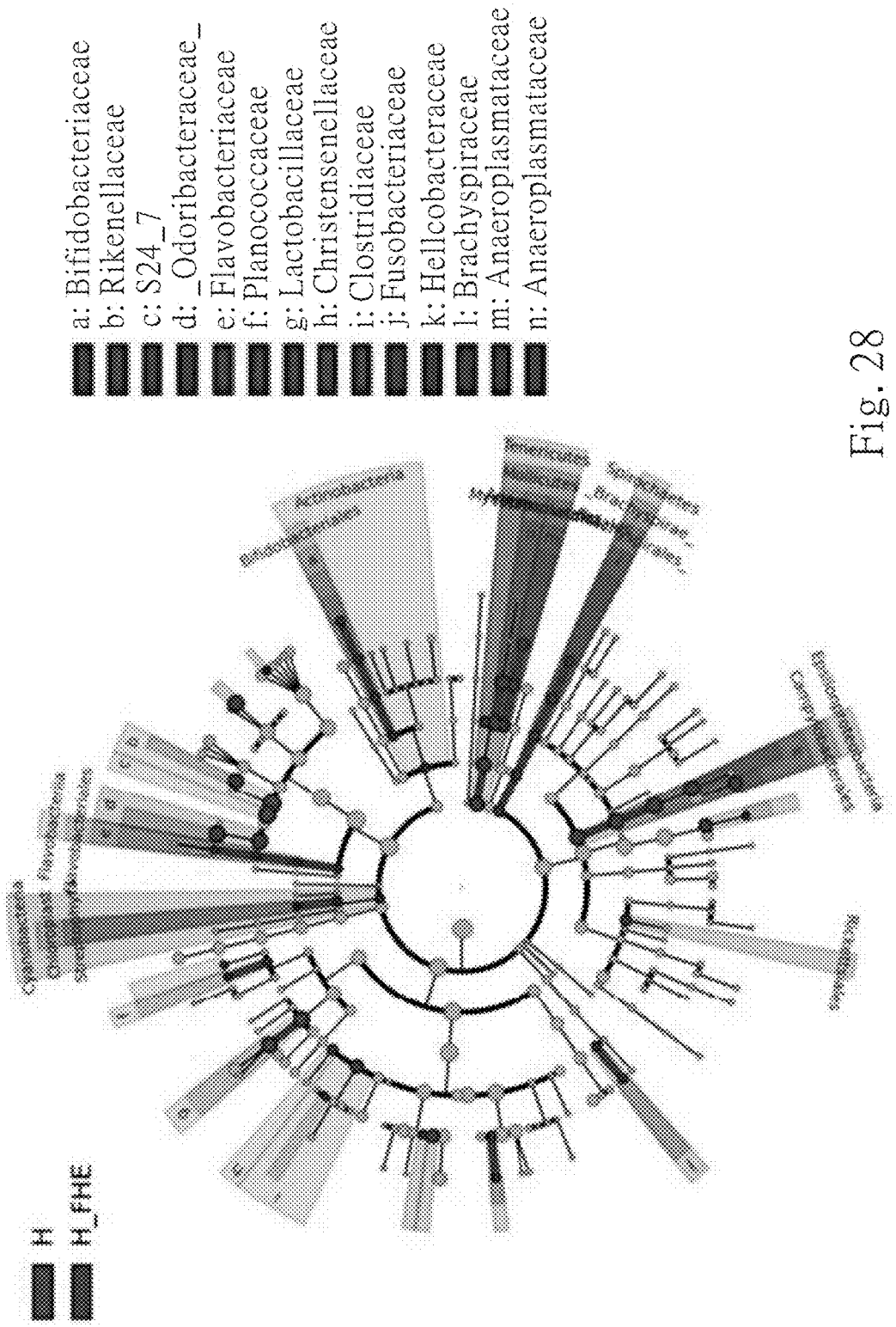
FIG. 28 shows the results of the gastrointestinal microbiota after the experiments of group H and group H_FNE of mice by the LefSe analysis.
Figure 29:
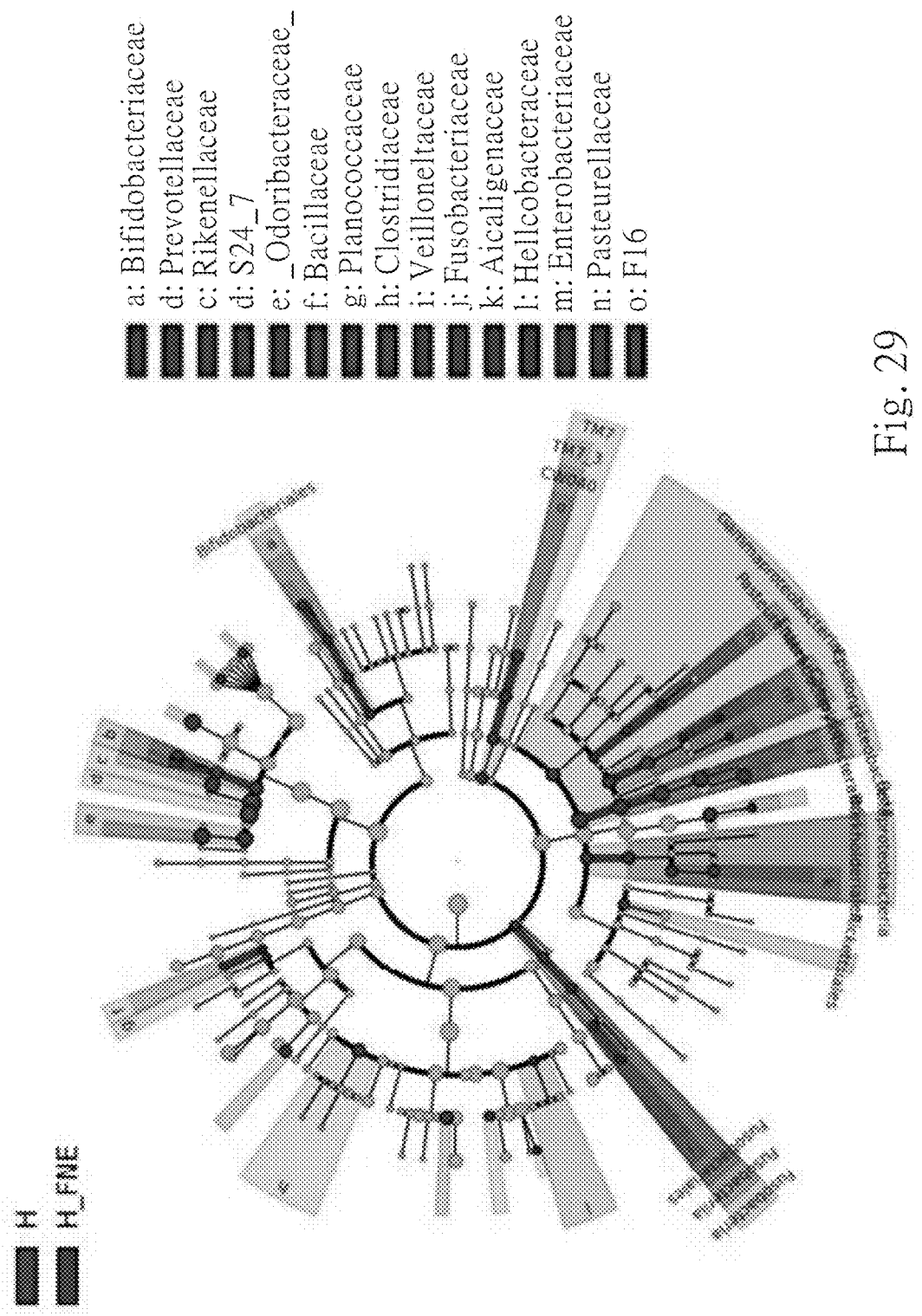
FIG. 29 shows the results of the gastrointestinal microbiota after the experiments of group H and group H_FNE of mice by the LefSe analysis.
Figure 30:
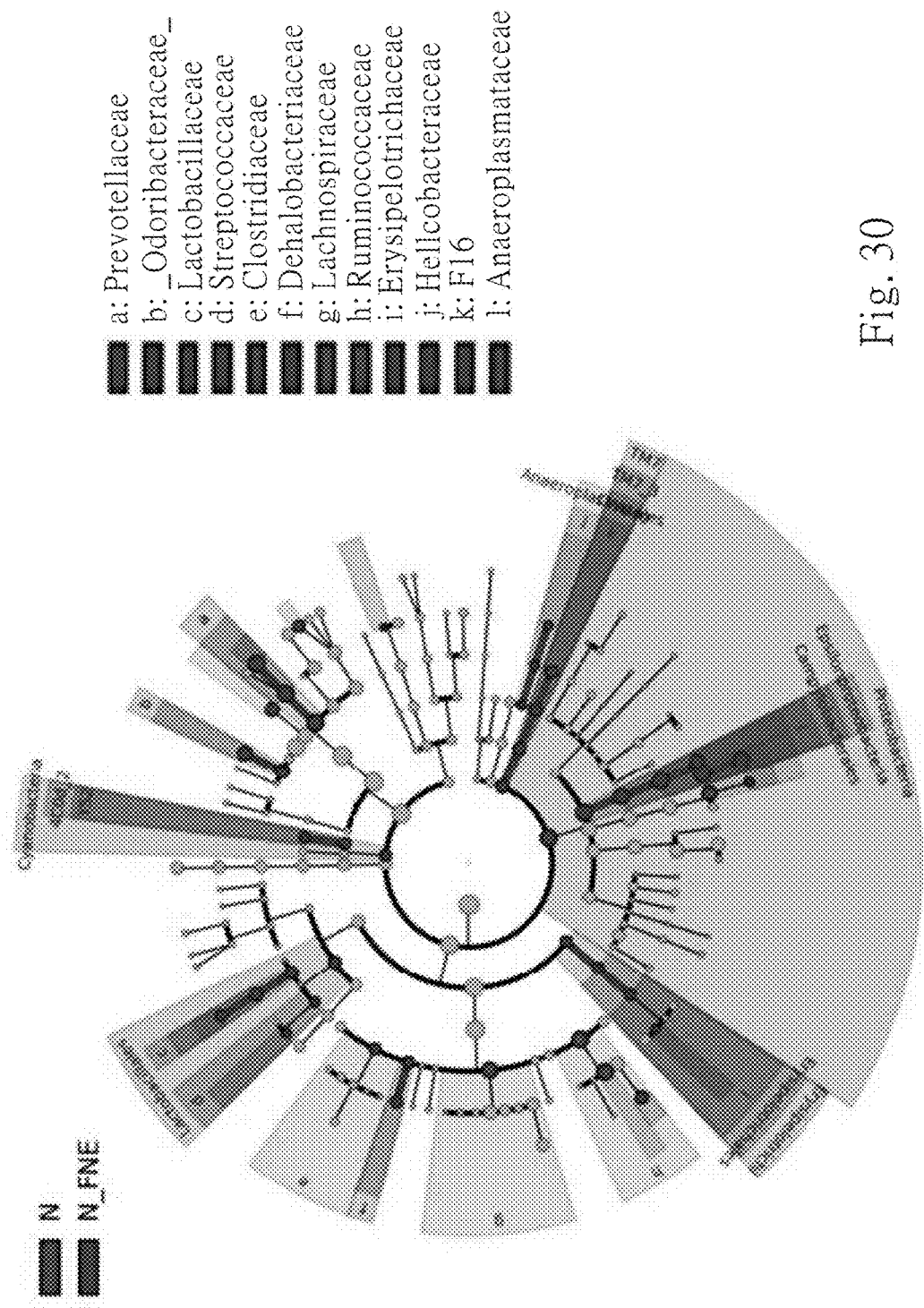
FIG. 30 shows the results of the gastrointestinal microbiota after the experiments of group N and group N_FNE of mice by the LefSe analysis.

The relative abundance of the gastrointestinal microbiota in each group of mice was further analyzed, as shown in FIG. 15 and FIG. 16. It is indicated from the results in FIG. 15 and FIG. 16 that an exercise habit or administration of a transplantation composition can increase the number of genera of the gastrointestinal microbiota in mice. Furthermore, after the experiments, the flora in groups H_FHE, H_FNE, HE, NE, and N_FNE includes additional genus *Helicobacter* and/or genus *Odoribacter* compared to those in groups N and H. In other words, a transplantation composition from a donor having an exercise habit includes bacteria of genus *Helicobacter* and/or genus *Odoribacter*, and when it is administered to a recipient, the gastrointestinal flora in the recipient can be added with bacteria of genus *Helicobacter* and genus *Odoribacter*. Therefore, it can be inferred that the presence of bacteria of genus *Helicobacter* and/or genus *Odoribacter* is associated with obesity, body fat, hepatitis, diabetes, blood glucose, and metabolic syndrome, indicating that a transplantation composition containing bacteria of genus *Helicobacter* and/or genus *Odoribacter* can effectively treat and/or prevent metabolic syndrome or related diseases thereof.

The differences in the gastrointestinal microbiota between groups of mice before or after the experiments were analyzed respectively with the LefSe analysis method, as shown in FIG. 17 to FIG. 30. The cladograms as shown in FIG. 17 to FIG. 30 show the taxonomic hierarchies among groups and the relative abundance size of each bacterium in each taxonomy. Further, a bar chart of log 2 (mean of group1)−log 2 (mean of group2) was made by choosing those having a significant difference of mean of relative abundance of greater than 0.001 in the taxonomic hierarchy of genus from the results after the experiments, and only top 10 having the maximum factor was listed, as shown in FIG. 31 to FIG. 33.

Figure 31:
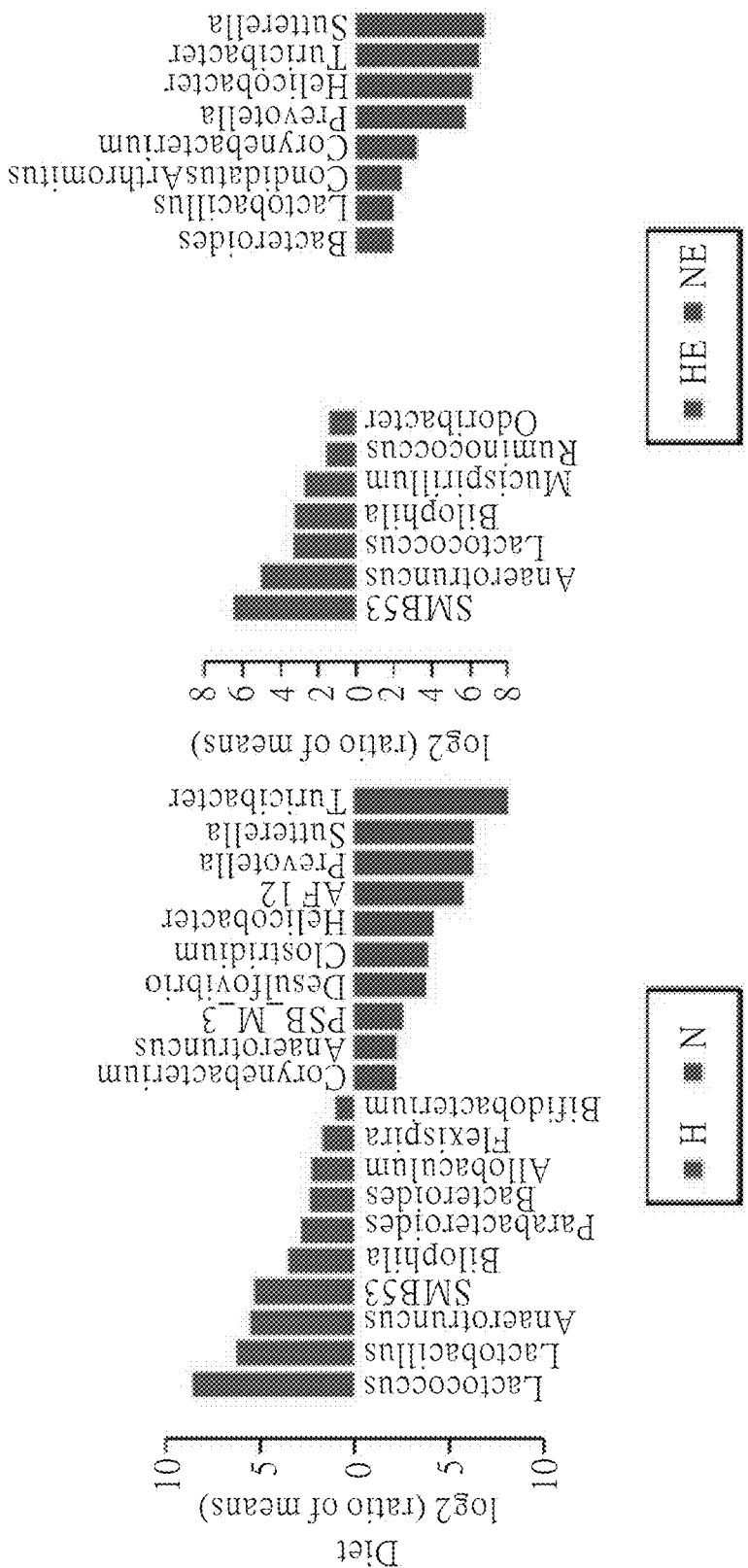
FIG. 31 is the results of comparison of genera of the gastrointestinal microbiota in mice of between groups H and N and between groups HE and NE.

The results in FIG. 31 show that compared to a high-fat diet group, a normal diet group has a higher number of bacteria of genus AF12 and genus *Helicobacter* in the gastrointestinal flora, and thus it can be known that bacteria of genus AF12 and genus *Helicobacter* are associated with obesity and metabolic syndrome related diseases.

Figure 32:
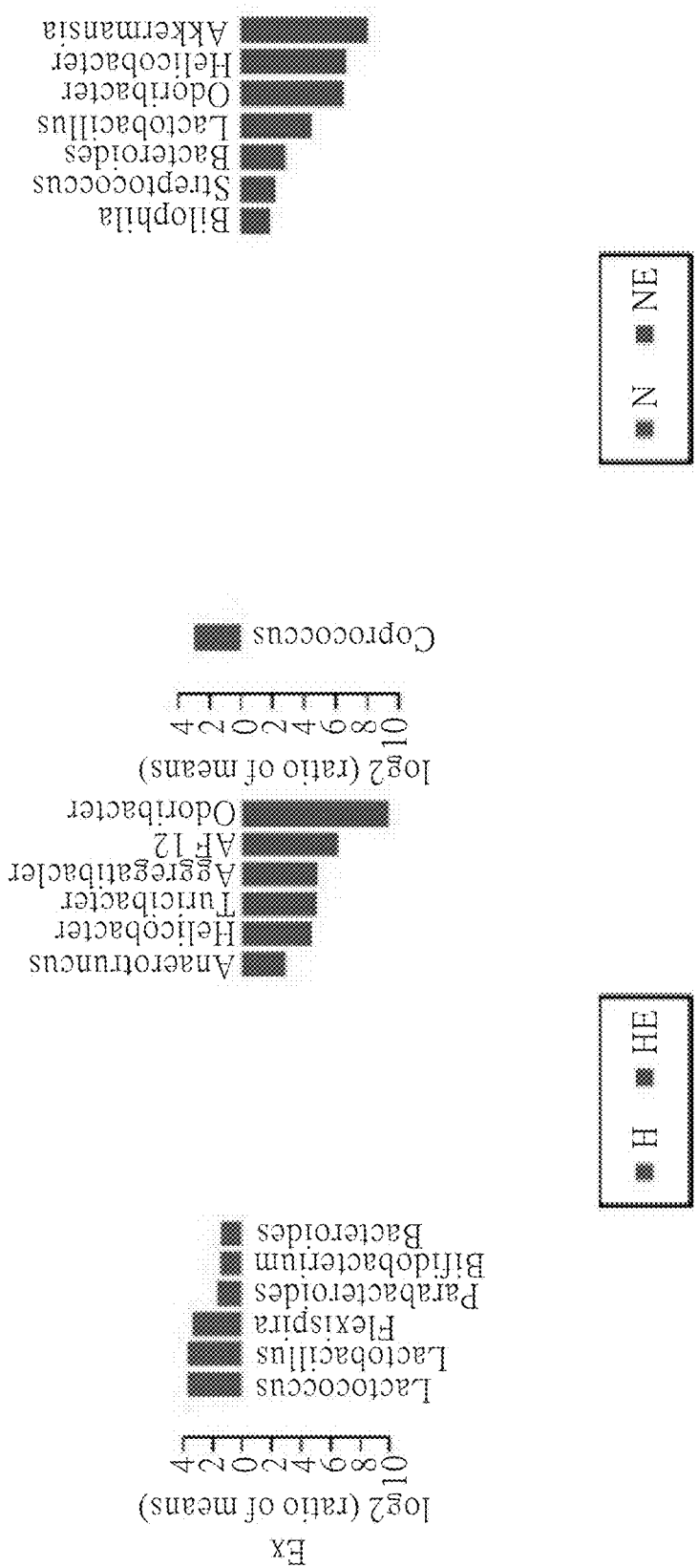
FIG. 32 is the results of comparison of genera of the gastrointestinal microbiota in mice of between groups H and HE and between groups N and NE.

Referring to FIG. 32, whether for a high-fat diet or a normal diet, where a predetermined exercise habit of an individual is maintained, the number of bacteria of genus AF12, genus *Helicobacter* and genus *Odoribacter* in the gastrointestinal flora can be increased, and for a high-fat diet, the increase in number of bacteria of genus AF12 and genus *Odoribacter* is more pronounced, while for a normal diet, the increase in number of bacteria of genus *Helicobacter* and genus *Odoribacter* is more pronounced. Thus, from the results in the previous examples, it can be known that bacteria of genus AF12, genus *Helicobacter* and genus *Odoribacter* can be correlated with improvement or treatment of metabolic syndrome and related diseases thereof, or reduction or prevention of occurrence of metabolic syndrome and related diseases thereof. In other words, increasing the number of bacteria of genus AF12, genus *Helicobacter* and genus *Odoribacter* can effectively prevent and/or treating metabolic syndrome and related diseases thereof.

Figure 33:
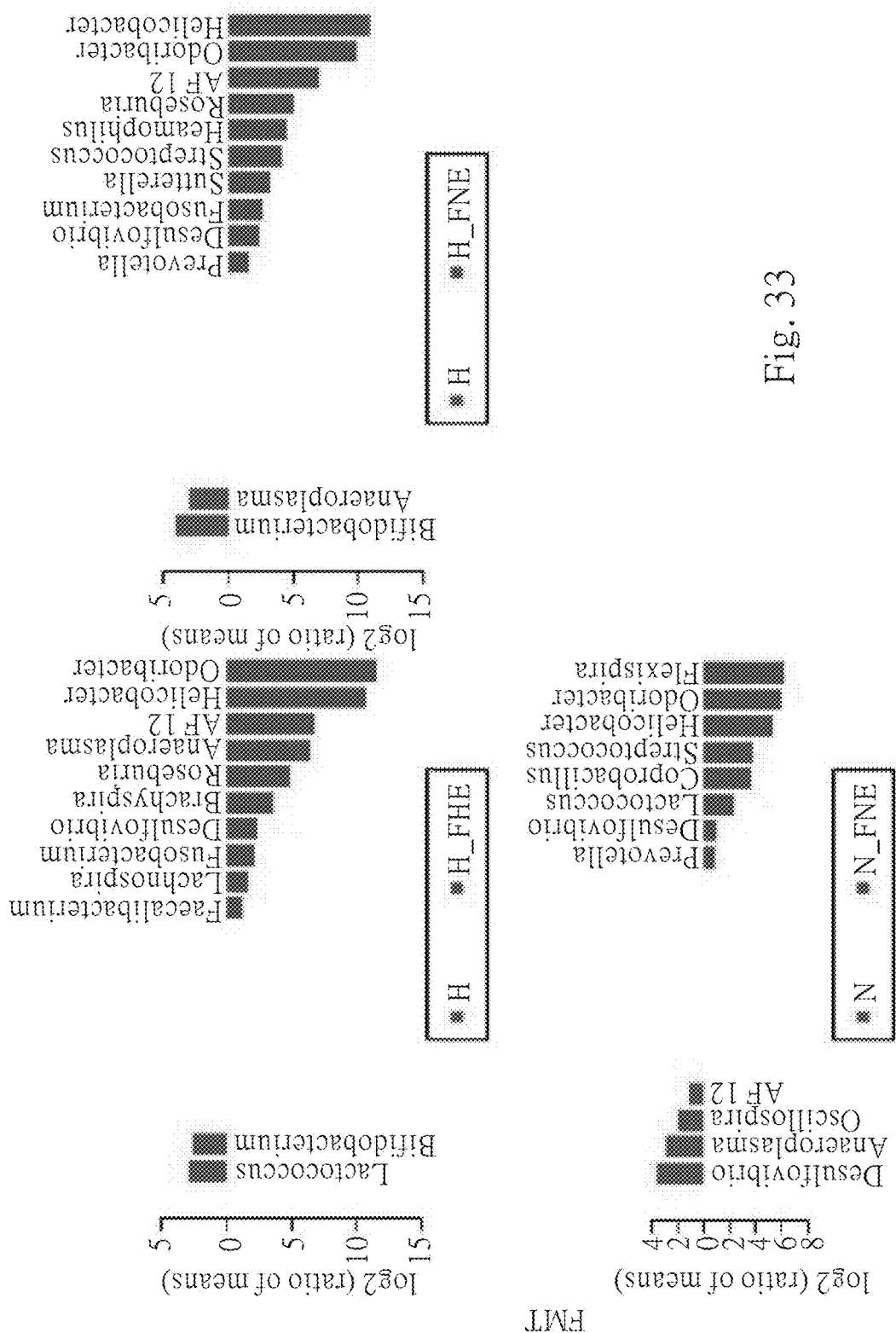
FIG. 33 is the results of comparison of genera of the gastrointestinal microbiota in mice of between groups H and H_FHE, between groups H and H_FNE, and between groups N and N_FNE.

It can be known from the results in FIG. 33 that administering a transplantation composition from a donor having an exercise habit, namely, one containing bacteria of genus AF12, genus *Helicobacter* and genus *Odoribacter*, to a recipient can add bacteria of genus AF12, genus *Helicobacter* and genus *Odoribacter* in the gastrointestinal flora of the recipient. From the results in the previous examples, it can be known that a composition containing bacteria of genus AF12, genus *Helicobacter* and genus *Odoribacter* can effectively improve and/or treating metabolic syndrome and related diseases thereof.

Example 10: Staining Analysis of Tissue Sections

The liver tissue and the fatty tissue of each group of mice were taken, embedded in paraffin, and sectioned. The liver sections of each group of mice were stained with H&E and Oil-Red respectively, and the adipose sections of each group of mice were stained with H&E. The staining results are shown in FIG. 34 to FIG. 36.

Figure 34:
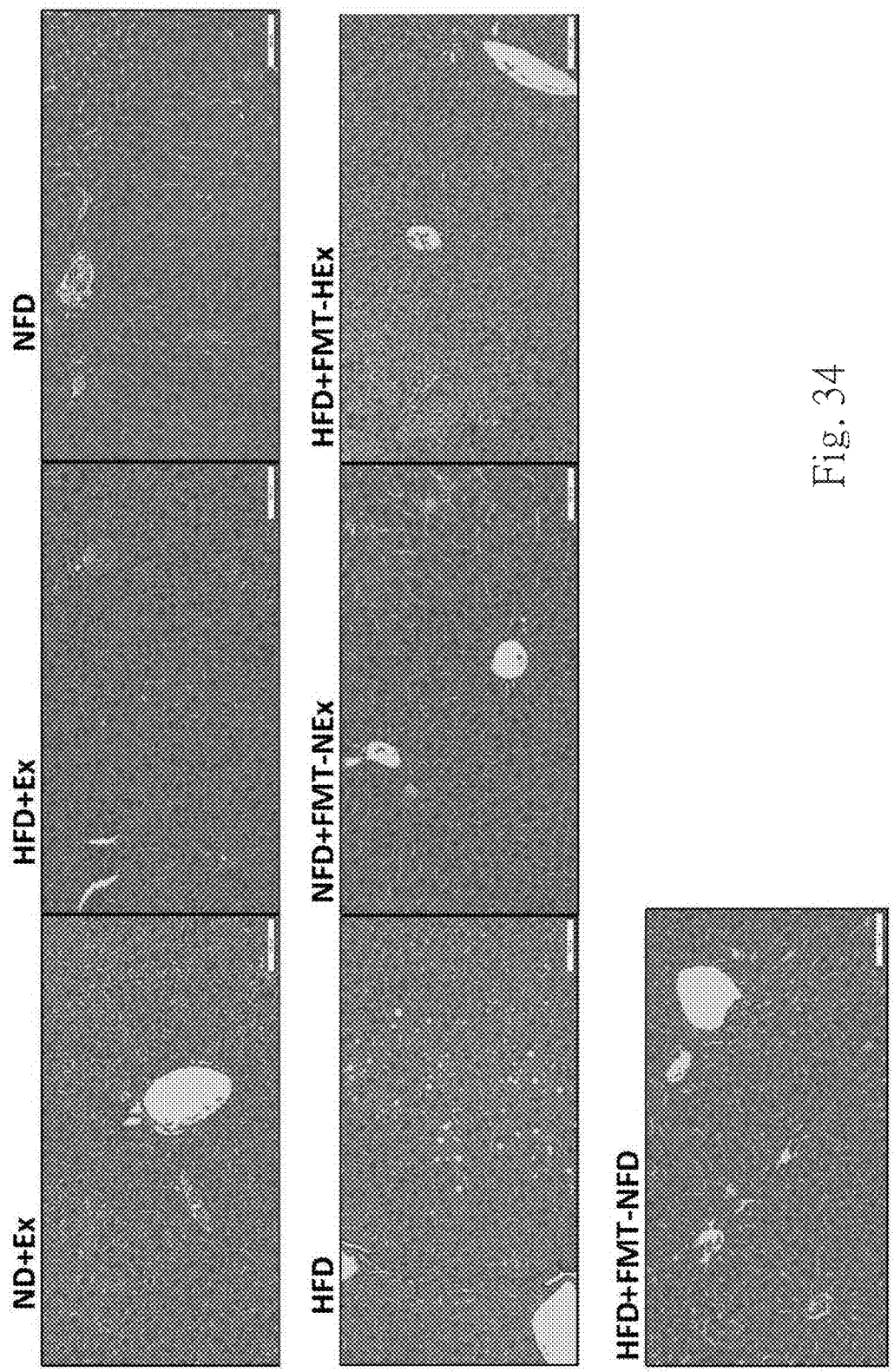
FIG. 34 is the results of H&E staining of liver sections of each group of mice.
Figure 35:
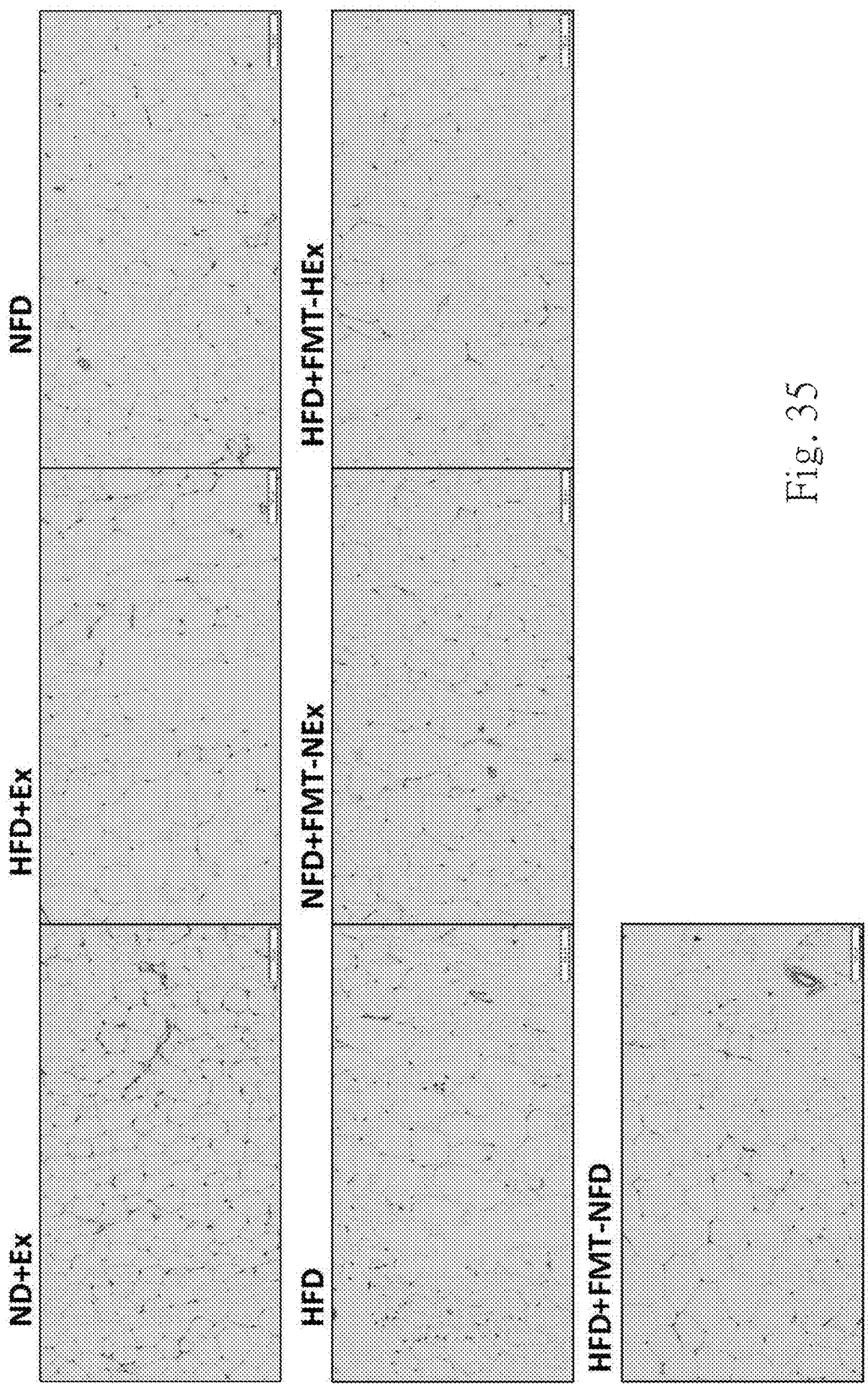
FIG. 35 is the results of H&E staining of adipose sections of each group of mice.
Figure 36:
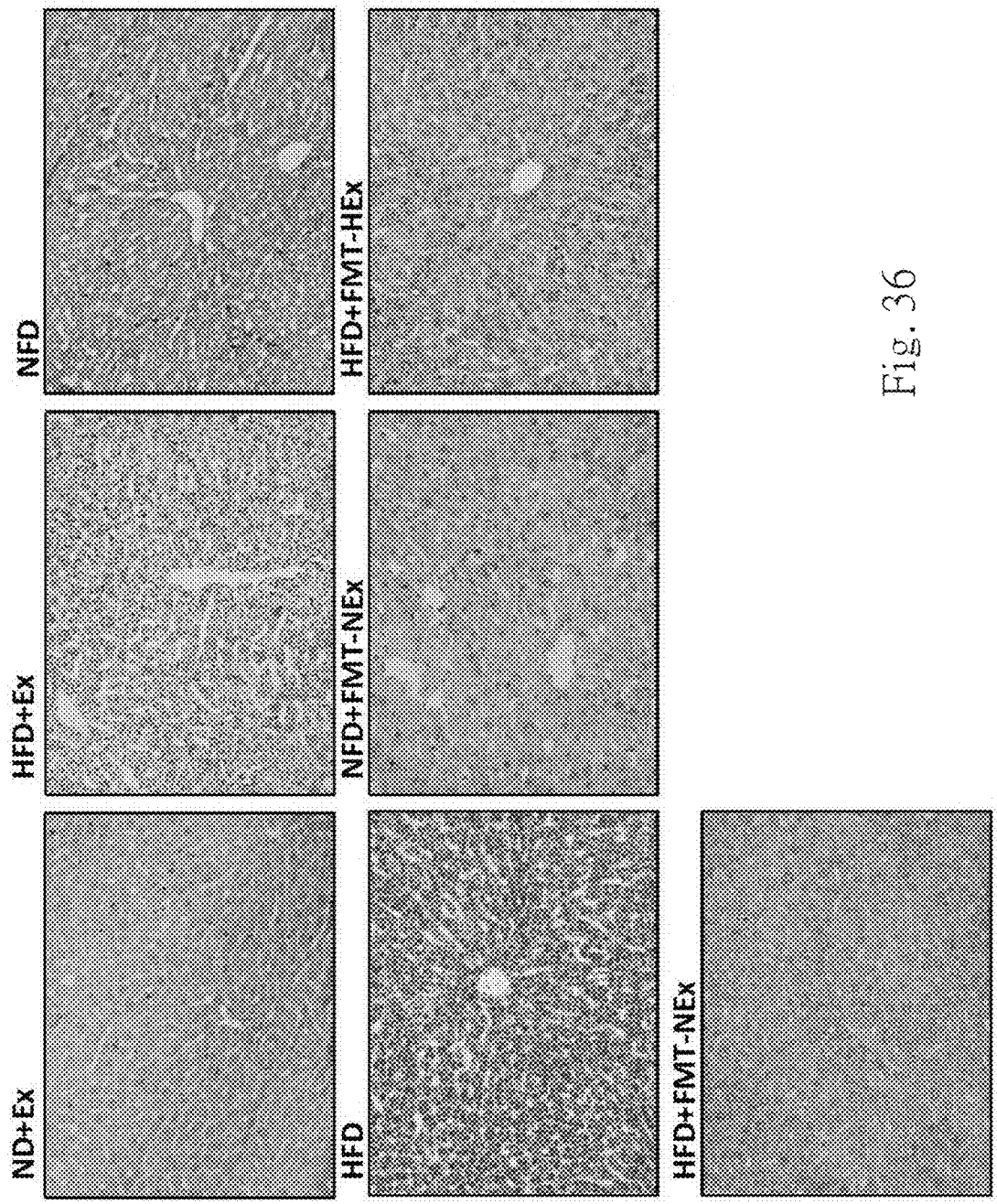
FIG. 36 is the results of Oil-Red staining of liver sections of each group of mice.

It can be known from the results in FIG. 34 to FIG. 36 that administering a transplantation composition from a donor having an exercise habit, namely, one containing bacteria of genus AF12, genus *Helicobacter* and genus *Odoribacter*, to a recipient can effectively improve the accumulation of fat in liver, thereby achieving the effect of treating or preventing fatty liver or related liver diseases thereof.

sufficiently increase the number of bacteria of at least one selected from the group consisting of genus *Helicobacter* and genus *Odoribacter* in the gastrointestinal tract of the individual to a level which treats and/or prevents obesity, regulating blood glucose, liver inflammation and reduces the level of low density cholesterol,
    wherein the composition is prepared from feces, which is derived from a donor having an exercise habit, and
    wherein the administration of the composition is via oral.

2. The method of claim 1, wherein the exercise frequency of the donor is selected from the group consisting of at least two exercises per week at above 30 min per exercise, and an exercise at above 75 min per week.

3. The method of claim 1, wherein the donor of the feces has a non-high-fat diet.

4. The method of claim 3, wherein the proportion of fat in a daily diet of the donor is less than 77%.

5. A method for treating and/or preventing obesity, regulating blood glucose, liver inflammation and reducing the level of low density cholesterol, comprising administering an effective amount of a composition to an individual to a level which treats and/or prevents obesity, regulating blood glucose, liver inflammation and reduces the level of low density cholesterol, the composition being derived from feces of a donor,
    wherein the donor has at least one condition selected from the group consisting of an exercise habit and a non-high-fat diet habit, and
    the administration of the composition is via oral.

6. The method of claim 5, wherein the exercise habit means an exercise frequency selected from the group consisting of at least two exercises per week at above 30 min per exercise, or an exercise at above 75 min per week.

What is claimed is:

1. A method for treating and/or preventing obesity, regulating blood glucose, liver inflammation and reducing the level of low density cholesterol, comprising administering an effective amount of a composition to an individual to 7. The method of claim 5, wherein the non-high-fat diet means that the proportion of fat in a daily diet of the donor is less than 77%.

8. A method for reducing body weight, comprising administering an effective amount of a composition to an individual to sufficiently reduce body weight, the composition being derived from feces of a donor, wherein:
   the donor has at least one condition selected from the group consisting of an exercise habit and a non-high-fat diet habit, wherein the administration of the composition is via oral.

9. The method of claim 8, wherein the exercise habit means an exercise frequency selected from the group consisting of at least two exercises per week at above 30 min per exercise, or an exercise at above 75 min per week.

10. The method of claim 8, wherein the non-high-fat diet means that the proportion of fat in a daily diet of the donor is less than 77%.

* * * * *